United States Patent
Goyal

(10) Patent No.: US 10,987,170 B2
(45) Date of Patent: Apr. 27, 2021

(54) SYSTEMS AND METHODS FOR ROUTING A VESSEL LINE SUCH AS A CATHETER WITHIN A VESSEL

(71) Applicant: MENTICE AB, Gothenburg (SE)

(72) Inventor: Mayank Goyal, Calgary (CA)

(73) Assignee: Mentice AB, Gothenburg (SE)

( * ) Notice: Subject to any disclaimer, the term of this patent is extended or adjusted under 35 U.S.C. 154(b) by 0 days.

(21) Appl. No.: 16/723,523

(22) Filed: Dec. 20, 2019

(65) Prior Publication Data

US 2020/0121395 A1    Apr. 23, 2020

Related U.S. Application Data

(63) Continuation of application No. 15/522,213, filed as application No. PCT/CA2017/050205 on Feb. 16, 2017, now Pat. No. 10,548,669.

(60) Provisional application No. 62/295,929, filed on Feb. 16, 2016.

(51) Int. Cl.
| | |
|---|---|
| A61B 34/10 | (2016.01) |
| G06T 17/10 | (2006.01) |
| G06T 11/00 | (2006.01) |
| A61B 34/20 | (2016.01) |
| A61B 5/103 | (2006.01) |
| A61B 34/00 | (2016.01) |

(52) U.S. Cl.
CPC .............. *A61B 34/10* (2016.02); *A61B 5/103* (2013.01); *A61B 34/00* (2016.02); *A61B 34/20* (2016.02); *G06T 11/003* (2013.01); *G06T 17/10* (2013.01); *A61B 2034/107* (2016.02); *A61B 2034/2065* (2016.02); *G06T 2200/08* (2013.01)

(58) Field of Classification Search
CPC ... A61B 2034/107; A61B 34/20; A61B 34/10; G06T 11/003
See application file for complete search history.

(56) References Cited

U.S. PATENT DOCUMENTS

| | | | |
|---|---|---|---|
| 2002/0137014 A1* | 9/2002 | Anderson | G16H 50/50 434/262 |
| 2007/0049861 A1 | 3/2007 | Gundel | |
| 2008/0171936 A1* | 7/2008 | Homan | A61B 6/547 600/424 |
| 2008/0183073 A1 | 7/2008 | Higgins et al. | |
| 2008/0207997 A1 | 8/2008 | Higgins et al. | |

(Continued)

FOREIGN PATENT DOCUMENTS

| | | |
|---|---|---|
| CN | 103961179 A | 8/2014 |
| EP | 1901232 A2 | 3/2008 |

(Continued)

OTHER PUBLICATIONS

Rahman S.U., Khalil A., and Alam F., A Review on Image Processing Based Optimal Catheter Selection in Coronary Angiography, The Journal of Cardiovascular Diseases, vol. 13(1), pp. 23-27 (2015).

*Primary Examiner* — Mainul Hasan
(74) *Attorney, Agent, or Firm* — McGlew and Tuttle, P.C.

(57) ABSTRACT

Systems and methods enabling a personalized solution for allowing more efficient access to the carotid artery (or vertebral arteries) m patients needing endovascular/neurointervention procedures using catheter systems.

6 Claims, 10 Drawing Sheets

(56) References Cited

U.S. PATENT DOCUMENTS

| | | | |
|---|---|---|---|
| 2008/0234700 A1* | 9/2008 | Trovato | A61B 90/10 606/139 |
| 2012/0173217 A1* | 7/2012 | Heimbecher | A61B 5/063 703/7 |
| 2012/0184844 A1* | 7/2012 | Gielen | A61B 6/5235 600/424 |
| 2012/0296620 A1 | 11/2012 | Aulbach | |
| 2015/0257847 A1 | 9/2015 | Higgins et al. | |
| 2016/0070436 A1* | 3/2016 | Thomas | A61B 6/032 715/771 |
| 2017/0079719 A1* | 3/2017 | Warner | A61B 5/055 |
| 2018/0225993 A1 | 8/2018 | Buras et al. | |

FOREIGN PATENT DOCUMENTS

| | | |
|---|---|---|
| EP | 3144834 A1 | 3/2017 |
| WO | 2015099427 A1 | 7/2015 |

* cited by examiner

-- Prior Art --

-- Prior Art --

-- Prior Art --

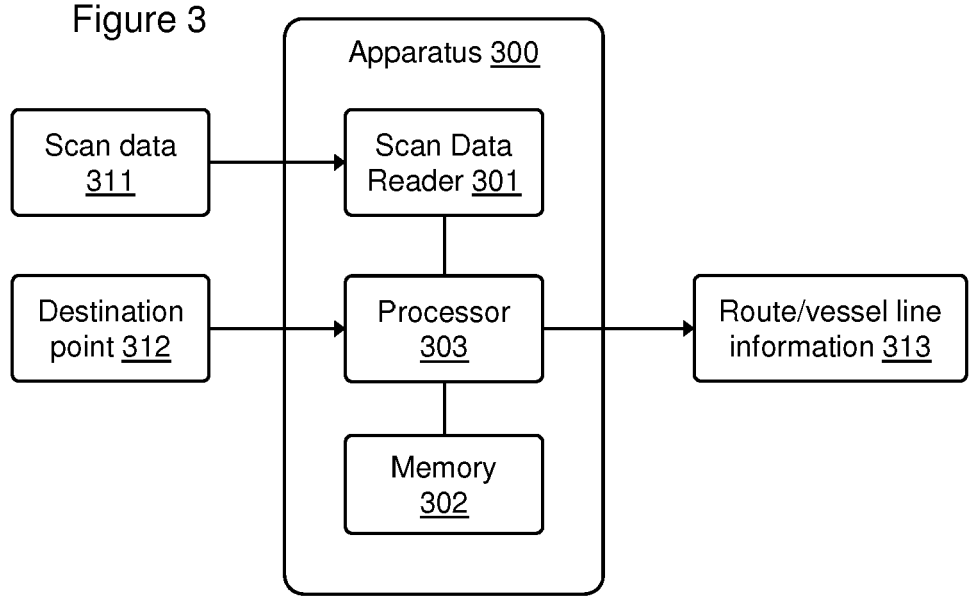
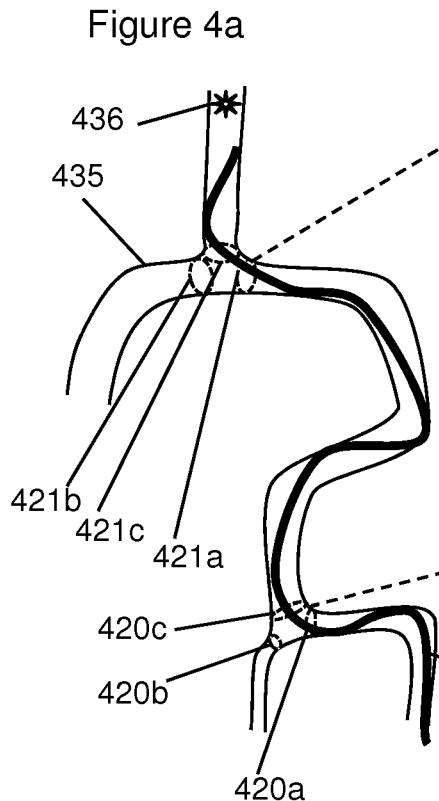
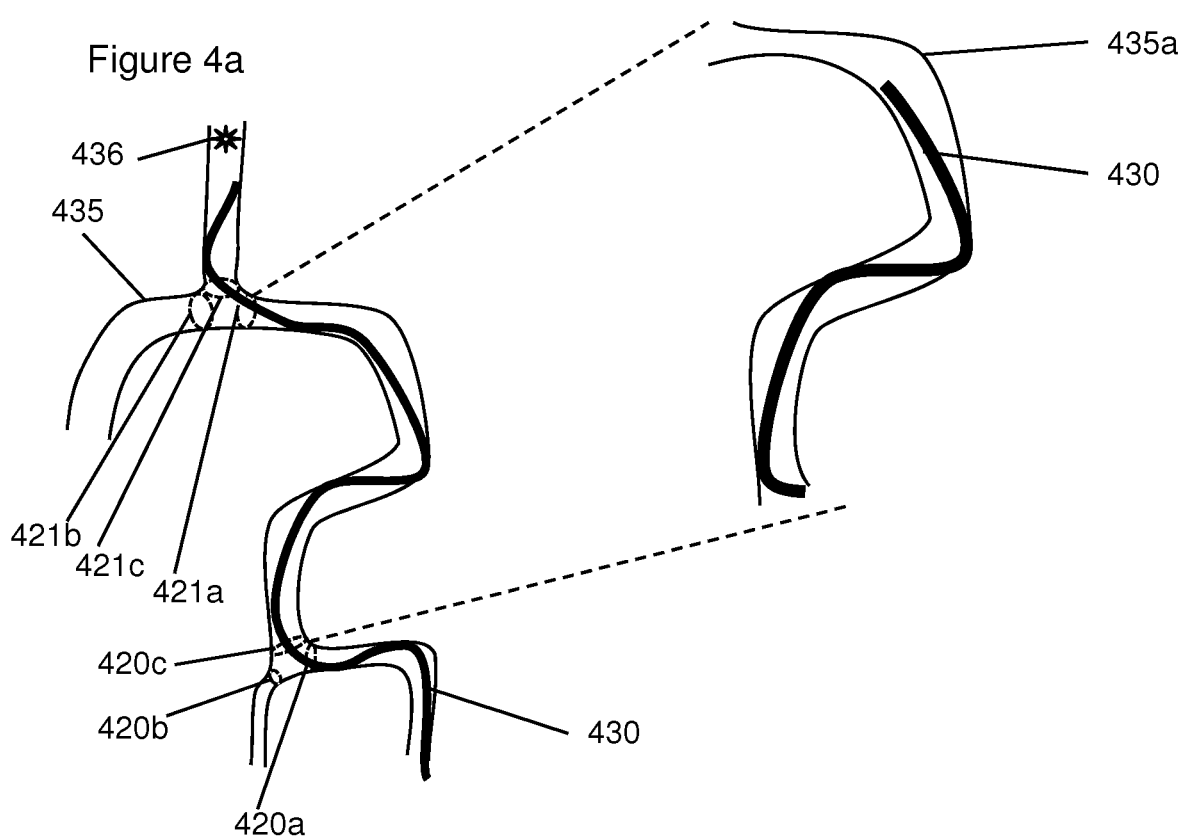

SYSTEMS AND METHODS FOR ROUTING A VESSEL LINE SUCH AS A CATHETER WITHIN A VESSEL

CROSS REFERENCE TO RELATED APPLICATIONS

This application is a continuation under 37 CFR 1.53(b) of pending prior U.S. patent application Ser. No. 15/522,213 filed Apr. 26, 2017, which claims the benefit (35 U.S.C. § 120 and 365(c)) of International Application PCT/CA2017/050205 filed Feb. 16, 2017 and claims the benefit of priority of U.S. provisional application 62/295,929 filed Feb. 16, 2016, the entire contents of each application are incorporated herein by reference, the entire contents of each application are incorporated herein by reference.

FIELD OF THE INVENTION

The invention relates to systems and methods enabling a personalized solution for allowing more efficient access to the carotid artery (or vertebral arteries) in patients needing endovascular/neurointervention procedures.

BACKGROUND OF THE INVENTION

As is known, the human or animal body has an extensive network of blood vessels including both the venous and arterial systems for circulating blood throughout the body as a whole as well as the organs of the body.

In recent years, a variety of traumatic surgical procedures have been replaced with procedures that involve the use of one or more catheters being advanced through the vascular system of the body to gain access to diagnose and/or treat issues involving the vasculature of a particular organ. For example, strokes (e.g. ischemic strokes caused by blood clot blockages in the brain); coronary artery blockages within the heart; and various heart defects may be treated by advancing catheters to the affected site where various procedures can be initiated to treat the problem. Stents have also been deployed via a catheter where such stents are positioned using catheters at a location where intervention is required. Other catheter procedures are also done in many parts of the body including leg vessels, renal arteries etc. as well as many other complex vascular percutaneous vascular procedures including for example treatment of valvular heart disease, aortic dissections, dysrhythmias, management of shunts for dialysis patients. Similarly complex aneurysms in the brain and other locations are increasingly being treated through a percutaneous endovascular route.

In order to effectively use catheters within the body to complete a medical procedure, generally the catheters must be flexible enough to follow through the tortuous curves of the body's vascular system whilst being stiff enough to hold position (e.g. when the interventionist passes additional tools through the catheter).

If the catheter is too flexible, the catheter may fall back into other vessels within the vascular system. If the catheter is too stiff, it may cause damage to the surrounding tissue as it navigates around corners of the vessels, if it is able to be moved at all and/or may cause significant time delays in completing the medical procedure. In certain procedures, such as endovascular interventions to remove a blood clot from the brain of a patient who has had an ischemic stroke, "time is brain", meaning that delays in completing a procedure can significantly affect the outcome for the patient.

Also, the degree of tortuousity within blood vessels as well as the stiffness of vessels increases with age due to multiple factors including atherosclerotic disease, loss of height of the spine, etc. With the aging population and improving technologies, more and more of these procedures are being done in an older population necessitating access despite the increased complexity of conducting procedures through tortuous and/or stiffer vessels.

Further still, there are significant variations in the vascular anatomy of different patients, FIG. 1 shows a typical aortic arch 179 and the connecting vessels in a human. The aortic arch 179 is connected to the ascending aorta 178 and the descending aorta 180. The ascending aorta is connected to the right and left coronary arteries 171, 172. The aortic arch is connected to the brachiocephalic artery 173 which splits into the right subclavian artery 174 and the right common carotid artery 175. Also connected to the aortic arch are the left common carotid artery 176 and the left subclavian artery 177. As noted, the figure shows a typical aortic arch but it will be appreciated that the precise connections and form of the vessels may vary from patient to patient. For example, in some patients, the left common carotid artery may arise from the innominate artery (this variant is called a bovine arch). In this situation the angle between the descending aorta and the left common carotid artery is more acute making the catheterization more challenging.

To take a typical catheter procedure as an example and as described in more detail below, to access the blood vessels in the head, the interventionist typically navigates a catheter system up the descending aorta 180 from the femoral artery and into the aortic arch 179 and into the left common carotid artery 176. For the purposes of the description herein a "catheter system" implies various combinations of inner catheters (eg. diagnostic catheters, guide wires, microcatheters) and outer guide catheters (eg. distal access catheters and balloon guide catheters) where the inner and outer components are substantially coaxial and can slide over or within the other. This can include coaxial, triaxial and rarely quadra-axial procedures. In most circumstances, the components will move together with a guide wire usually extending beyond the outer guide catheter and inner components such as a diagnostic or microcatheter. Hence, the catheter system may be both a combination of a wire within the catheter during antegrade movement of the catheter system but may also mean just the catheter without the wire. Antegrade movement is generally conducted by a combination of advancing the guide wire followed by advancing the catheter over the wire all of which may involve twisting or turning the catheter and wire in order to turn the distal end of the guide wire and catheter into the appropriate vessel. After reaching the aortic arch, for example, the catheter system is navigated up the left common carotid artery 176 and into the left internal carotid artery. Depending on the underlying condition and the procedure being conducted, at this stage the interventionist may utilize a variety of different catheters (including microcatheters and microwires) and techniques to gain access to intracranial vessels and ultimately to the site where the procedure is to be conducted.

As Figure1 indicates, the vascular system comprises complex junctions in which a number of vessels intersect. In addition, older people often have increasing tortuosity and/or stiffness of their vessels and also the vessels may become longer. A catheter system which is too stiff can straighten out tortuous vessels (which mayor may not be advantageous) and/or produce damage to the vessel as it is being navigated through a tight curve. However, if the catheter is too flexible, it may not be able to maintain its position within the vessel and, for example, fall back into the aortic arch after it has been successfully guided into the left internal carotid artery (especially as further catheters and tools are being advanced through the catheter to enter the brain vessels and/or as the guide wire is withdrawn). In some cases additional catheters face friction as they are being advanced and as such, this creates a backward force on the guiding catheter hence preventing the interventionist from completing a procedure and/or wasting time in removing a catheter and selecting and navigating a different catheter into position.

Catheter Design and Performance

As noted above, two classes of catheters used in cerebral procedures are diagnostic and guide catheters. Diagnostic catheters are generally those used to gain access to an area of interest whereas guiding catheters are used to support and guide additional equipment including diagnostic catheters, guidewires, balloons, other catheters etc. as may be required for a particular surgical technique.

Typical diagnostic catheters will range from 4 F to 6 F (French) and have lengths of 65-125 cm. They may have braided wall structures and they will generally have a soft tip with a range of shapes formed into the tip.

Guide catheters are generally larger (eg. 6-8 F) and are 80-100 cm in length. They generally have reinforced construction with a significantly stiffer shaft to provide back-up (i.e retro) support for the advancement of any additional equipment as mentioned above.

From an anatomical perspective, catheters generally pass through different zones of the vasculature, namely the abdominal and thoracic vasculature between the femoral artery and aortic arch (approximately 50-75 cm), the cervical vasculature (approximately 15-20 cm) and the cephalic/cerebral vasculature (approximately 10-15 cm).

Various properties and geometries may also be engineered into both diagnostic and guide catheter including:

a. Trackability—the ability of the catheter to slide over a guide wire particularly through tortuous (tightly curved) vessels.
b. Pushability—the ability to advance the tip or head of the catheter based on the input from the operator from the hub (i.e. from outside the body).
c. Torquability—the ability to steer the tip of the catheter based on twisting at the hub by the operator.
d. Tip or head shape—the shape of the tip or head of the catheter will assist the operator in navigating the distal tip of the catheter through particular anatomical features. For example, a catheter may have a flush, straight, simple curve, complex curve, reverse curve or double curve shapes inter alia. Such shapes may be categorized as simple or complex.

In particular, diagnostic catheters are provided with a wide range of tips having the above shapes to allow the surgeon a choice of tip shape when conducting a procedure mainly to address variations in a patient's anatomy.

Catheter Construction

Each catheter may be constructed from a plurality of materials, having various structures and/or layers within the catheter wall structure to give the catheter particular properties or functional characteristics. These may include:

Surface Coatings—Surface coatings desirably reduce thrombogenicity, have low friction coefficients and/or anti-microbial characteristics.

Reinforcement—Internal wire braiding is used to impart torque control/stiffness characteristics to the catheter.

Polymer Layers—Different polymers may be used to give different structural characteristics to the body of the catheter. For example, Polyurethanes can be soft and pliable and hence follow guide wires more effectively. However, they have a higher coefficient of friction.

Nylon may be used for stiffness and be able to tolerate higher flow rates of fluids through them.

The choice of a particular catheter or system of catheters may be determined by the skill and experience of a particular surgeon.

Some typical properties of different catheters are summarized in Table 1.

TABLE 1

Summary of Catheter Properties

| Catheter | Body Properties | Diameter | Typical Length | Typical Tip Features |
|---|---|---|---|---|
| Guide Catheter | Usually quite stiff Atraumatic tip Supports and guides other catheters Double lumen if Balloon Guide Catheter (BGC) | 6-8F | Extracorporeal + Groin to Carotid 80-100 cm | May have balloon |
| Diagnostic Catheter | Variable Tip Stiffness Variable Tip Shapes Torquable | 4-6F | Extracorporeal + Groin to Carotid 100-125 cm | Soft Tip Multiple Shapes |
| Microcatheter | Soft Tip Pushable Trackable | 1-5-2.5f | Goes through the guide catheter Travel to intracranial | Rounded Soft Tip |

TABLE 1-continued

Summary of Catheter Properties

| Catheter | Body Properties | Diameter | Typical Length | Typical Tip Features |
|---|---|---|---|---|
| | | | vessels (over a microwire) and to beyond the clot. 150 cm | |
| Guide Wire | Pushable Torquable | 1F | Travels inside of diagnostic catheter or guide catheter (used to advance these catheters to the cervical carotid artery) 150-300 cm | Rounded |
| Reperfusion Catheter | Multizone (may be up to 12-15 zones) Increasing level of softness distally to allow the catheter to negotiate significant tortuosity and remain atraumatic Distal transition zones may extend for 30-40 cm) Enables two-way Fluid Flow Pushable | 4-6F (diameter may be more proximally to allow for better suction. | Travel inside the guide catheter. Usually over a microcatheter Extracorporeal + Groin to Occlusion 105-125 cm | Rounded Soft Tip Challenging design to prevent ovalization during passing through significant curvature and while applying suction. |
| Stent | Integrated Clot Retrieval System Pushable | very small in its collapsed state (travel through microcatheter). In expanded state: 3-6 mm | Extracorporeal + Groin to Occlusion 180 cm Travel through microcatheter. | Integrated Clot Retrieval System |
| Microwire | Pushable Torquable 10-16/1000 of an inch soft atraumatic tip | 180-200 cm travels through microcatheter | extracorporeal to intracranially (beyond the clot) | round soft tip. |

Typical Endovascular Procedures for Treatment of Ischemic Stroke

As noted above, when an endovascular surgeon begins a procedure, access to the vasculature is typically obtained through the groin. After groin puncture, a variety of the following steps are performed to advance different catheters through the vasculature to a site of interest. Typically, in the case of a procedure using a balloon guide catheter and stent (i.e a clot retrieval device), these steps include:

Step A—Aortic Arch Access a. Following groin puncture, a sheath is deployed. The sheath acts as an access port to the body and will be inserted about 5 cm of a typical 15 cm length into the femoral artery. The sheath has an 10 of approximately 8 F.

b. An assembly of a balloon guide catheter (BGC), a diagnostic catheter (DC) and guide wire (GW) is advanced to the aortic arch. The BGC will typically have an OD of 8F. The DC (OD 4-6 F) is retained inside the BGC and the GW (OD 0.035") is retained within the DC.

Step B—Carotid and Cerebral Artery Access c. The DC is manipulated to gain access to the desired carotid artery.

d. After gaining access to the carotid artery, the GW is advanced, typically up to 20-30 cm towards the occlusion site (but within the cervical carotid arteries).

e. After the GW has been advanced (or concurrently and/or sequentially), the DC is advanced over the GW to gain access to the occlusion site. This may occur in a concurrent and/or sequential process depending on the particulars of a particular patient.

Step C—Balloon Guide Catheter (BGC) Placement
  f. The BGC is advanced over the DC and GW to also gain access to a straight segment of the cervical internal carotid artery.
  g. The DC and GW are then fully removed.
Step D—Microcatheter/Microwire placement
  h. A microcatheter (MC) and microwire (MW) are advanced together through the BGC all the way to the clot such that the distal tip of the MC and MW are positioned just past the distal edge of the clot.
  i. Once the MC is positioned, the MW is removed.
Step E—Stent Deployment
  j. A stent (i.e. clot retrieval device) is advanced through the MC until the distal tip of the stent is adjacent the distal end of the MC.
  k. The stent is unsheathed by pulling back on the MC while holding the stent in position. As the stent is unsheathed it will expand into clot to engage with the clot.
Step F—Clot Removal
  l. The BGC is inflated to stop antegrade flow and retrograde flow (suction) through the BGC is initiated.
  m. Simultaneously, the stent which is now engaged with the clot, together with the MC is pulled proximally through the BGC to outside of the body.
  n. A check angiogram is performed through the BGC to see if the clot retrieval has been successful. If not the steps j-m may be repeated again.
  o. Once successful reperfusion has been achieved the BGC, stent and clot are removed from the body.

In variations of the procedure, a distal access catheter (DAC) (4-6.5 F) may be added to the procedure. This can be done one of two ways a. Aspiration technique.
    i. In this technique, after access to the cervical internal carotid artery has been achieved using a guide catheter and DC, the guide catheter (GC) which is not a BGC (i.e a DAC) is placed in the cervical internal carotid artery.
    ii. The DC is removed
    iii. A tri-axial system consisting of a DAC, a MC and MW are advanced towards the intracranial circulation with the aim of having the tip of the DAC (Aspiration catheter) reach the face of the clot. For achieving this it is possible that the MC and MW may have to be placed beyond the clot.
    iv. The MW and MC are removed.
    v. With the DAC at the face of the clot, suction through the DAC is applied until there is successful retrieval of clot or the endovascular surgeon decides to try an alternative approach. Local suction has an advantage that more of the suction pressure is likely to be transmitted to the clot.
  b. Solumbra technique
    i. The initial part of this technique is the same as the Aspiration technique (i.e steps a(i)-a(iii)).
    ii. However once the MC is beyond the clot and the DAC is at the face of the clot, the MW is removed and a stent is deployed across the clot.
    iii. Then, while applying suction to the DAC, the MC and stent are withdrawn. Thus, the suction pressure is right next to the clot rather than from the neck as with a BGC. Also, the stent enters the DAC while still in the intracranial vessels thus reducing the likelihood of losing the clot once it has been captured.

In cases where the aspiration techniques without using a stent are not successful in removing the clot, with a BGC in place, a GW, MC and stent may be subsequently deployed.

Importantly, during any procedure the physician must carefully balance differences in the various geometrical and physical parameters of the catheter system against the 3 dimensional geometry of the patient's vasculature. That is, the physician must consider, for example, the shape of the distal end of the diagnostic catheter system with the understood geometry of the patient's vasculature, the stiffness of the guide catheter as well as the procedural objective of the catheter system as a whole.

Generally, a variety of diagnostic catheters are available to the physician where a particular diagnostic catheter is chosen depending on the route desired and the location of the issue. While a physician may have a significant number or library of diagnostic catheters available to him/her for a particular procedure, the selection of a particular catheter will often be based on the physician's experience and/or interpretation of the patient's vasculature from diagnostic and/or imaging results. As noted above, other factors, including the patient's age and size may also be considered. For example, when considering the imaging data, the physician may interpret particular features of the image that suggest the use of one diagnostic catheter design over another. That is, to the skilled eye of the physician, imaging data may reveal a degree of tortuosity with the vasculature that would suggest using a guide catheter having a more flexible region to enable navigation around a particularly tight curve to avoid the time delays that may result if a guide catheter that is too stiff is selected. However, a guide catheter that is too flexible may present problems during the procedure if it is unable to properly support microcatheters, microwires and other equipment within it for subsequent steps of the procedure. Further still, as shown in FIGS. 2A and 28, different tip shapes of a DC can be selected which are ideally matched to the shape of the patient's vasculature in order that the interventionist can "hook" the vessel of interest with the appropriate DC. As can be appreciated, the ultimate success and speed by which a physician can place the DC is the result of various factors including balancing the degree of forward push, the torque applied to the DC and the selection of the right device against the actual anatomical factors. Importantly, throughout the process various complexities can occur where the DC does not go into the vessel of interest but ends up somewhere else.

As such and as can be appreciated, training to become skilled at catheter placement is an involved process requiring many hundreds or thousands of hours of practice, mentoring and exposure to a wide range of patients and their respective anatomies whilst carrying out a wide range of procedures. However, the process of medical training is a process of graded responsibility wherein senior established physicians slowly allow trainees to do increasing amounts of patient management. However in the case of many emergencies, particularly those that are as emergent and complicated as acute stroke, there are limitations in terms of how much opportunity a trainee gets. As a result, while medical trainees may be exposed to complicated procedures, the amount of hands on experience they acquire during these emergencies may take many years to acquire.

Furthermore, in the case of acute stroke, it is well accepted that 'time is brain' with there being clear data to support that the faster the brain is repurfused, the higher the likelihood of a better outcome for the patient. As such during the management of an acute stroke, all the steps of recanalization described above should be conducted as fast as possible. This includes imaging, image processing, diagnosis, patient preparation, and the actual steps of a procedure.

Training systems exist that can assist the physician in developing their skills including simulation systems that interface physical manipulation of a real proximal end of a catheter system to a simulation of the distal end within a simulated vasculature. Such systems, for example, as described at www.mentice.com. provide physicians an effective way of developing manual manipulation skills and experience with a simulated system which can significantly improve skill levels prior to real-world procedures on patients.

While effective, current simulators are limited in that while they simulate "real" patient anatomies, derived from real imaging data, they do not represent the anatomies of an actual patient who is in immediate need of a procedure. That is, while current simulation systems allow physicians to practice on simulated patients, they are not actual patients whose specific anatomies are before them. Moreover, while a physician may be able to practice on various simulated patients with known variations and complexities in their anatomy, such practice may have become dated by the time an actual patient presents having a particular anatomy. That is, it may have been months or years since the last time a physician practiced on a particular anatomy.

The inventor's papers (incorporated herein by reference) "Analysis of Workflow and Time to Treatment on Thrombectomy Outcome in the Endovascular Treatment for Small Core and Proximal Occlusion Ischemic Stroke (ESCAPE) Randomized, Controlled Trial" (Circulation. 2016; 133: 2279-2286. 001: 10.1161/CIRCULATIONAHA.115.019983) and "Analysis of Workflow and Time to Treatment and the Effects on Outcome in Endovascular Treatment of Acute Ischemic Stroke: Results from the SWIFT PRIME Randomized Controlled Trial" (Radiology; 2016) discuss the variances in different steps of the workflow from the onset of an ischemic stroke to completion of recanalization procedures. As shown from these studies and as shown in Table 2, there is significant variation in the time that a surgeon may spend to complete a recanalization procedure.

TABLE 2

Interval Times in the Workflow of the ESCAPE Trial

| Workflow Time Intervals | N* | Median, min | Interquartile Range |
| --- | --- | --- | --- |
| Stroke system onset to arrival in emergency department of endovascular-capable hospital | 308 | 107.5 | 49.5-224 |
| Stroke symptom onset to qualifying CT | 311 | 135 | 76-244 |
| Stroke symptom onset to randomization | 314 | 174 | 119-285 |
| Stroke symptom onset to first reperfusion | 145 | 241 | 176-359 |
| Arrival in emergency department of endovascular-capable hospital to qualifying CT | 311 | 19 | 11-29 |
| Qualifying CT to groin puncture | 161 | 51 | 39-68 |
| Groin puncture to first reperfusion | 144 | 30 | 18-45.5 |

From these studies, variances in the time to complete particular steps can be attributed to different factors including the skill and experience of the surgeon, the equipment that may be used and the anatomy of the patient. Thus, to the extent that resources are available that enable the training of surgeons, the identification of equipment that may be most appropriate for a particular patient and/or recognition of particular characteristics of a patient's anatomy, time to reperfusion can be reduced and/or the variances in these times on a wider scale can be reduced or improved.

Accordingly, there has been a need for systems and methods that address these problems and more specifically for systems and methods that improve the skills and decision making of surgeons. Moreover, there has been a need for providing a personalized solution for the surgeon to practice on the actual patient that, within a few minutes, they will actually be conducting a procedure on. That is, there is a need for systems that utilizes CT scan and/or other imaging data obtained from a patient during a diagnostic phase that can be used within a simulator while a patient is being prepared for an endovascular procedure in order to assist the surgeon in pre-selecting specific catheters/equipment for a procedure, whilst also enabling them to practice the placement of selected catheter equipment within that specific patient's anatomy.

Furthermore, there has been a need for systems that, based on the specific anatomy of a patient, suggests and/or selects one or more recommended pieces of equipment having knowledge of the procedure about to be performed and a library of available equipment.

Further still, there has been a need for systems that based on the specific anatomy of the patient, suggest alternate techniques based on historical data if the geometry/characteristics of a particular anatomy has been shown in the past to be problematic to one particular procedure.

Further still, there has been a need for systems that based on the experiences of physicians conducting procedures using particular catheters within particular anatomies can recognize past situations and provide tips or insights to a physician when they are conducting a procedure which presents circumstances similar to a previously conducted procedure.

Further still, there has been a need for systems that can utilize the data of past procedures to assist in the design of future equipment having consideration to procedures that may have experienced problems.

Further still, there has been a need for systems that allows the manufacturers of catheters and wires to test their products against various anatomical variations to design and improve their products.

Further still, there has been a need for systems that can allow a physician to record an actual procedure and feed it back into a simulation system having an interactive environment to understand how procedures could be done differently or better.

SUMMARY OF THE INVENTION

In accordance with the invention, there is provided systems and methods for improving the efficiency of surgical procedures using catheter systems to move from an entry point to a location in the body where a treatment or diagnostic procedure may be completed.

In a first aspect, an apparatus is provided having: a scan data reader configured to determine the course of a vessel within a body based on a scan of the vessel; memory configured to store the physical properties of one or more vessel lines; a processor configured to determine: an route to reach a destination point within the vessel using a vessel line based on the determined vessel course, and whether it is possible to reach the destination point for each of the stored vessel lines.

In one embodiment, the processor is configured to determine the external manipulations required to cause the vessel line to follow the determined route.

In another embodiment, the apparatus is configured to determine the level of difficulty to reach a particular point within the blood vessel based on multiple different vessel lines; and determine which of the vessel lines has the lowest level of difficulty.

In another embodiment, the apparatus is configured to determine the parameters of a vessel line which is matched to the determined route of the blood vessel.

In another embodiment, the vessel line physical properties comprise a combination of one or more of: thickness; transverse elasticity; longitudinal elasticity; transverse stiffness; longitudinal stiffness; resting configuration; and one or more activated configurations.

In yet another embodiment, the apparatus comprises a scanner configured to scan a blood vessel to provide the scan data.

In yet a still further embodiment, the apparatus is configured to scan the blood vessel, read the scan data and determine the route in real time.

In another embodiment, vessel junctions are modelled by entrance and exit areas through which the vessel line must pass in order to enter a particular vessel portion from the junction.

In another embodiment, the apparatus is configured to output results of determination to replicate the feedback provided by a scanner during a medical procedure.

In yet another embodiment, the apparatus is configured to determine a measure of the difficulty to reach the destination point using a particular vessel line based on the physical properties of the particular vessel line and on the course of the vessel.

In another aspect, a method for improving the efficiency of surgical procedures conducted using catheter systems is described, where the surgical procedure includes navigating a catheter system through a patient's vasculature from an entry point to a destination, the method including the steps of: conduct a scan of a patient to obtain patient specific image data of the patient's vasculature; and using a non-transitory computer readable medium encoded with instructions to perform the following steps: construct a 3-dimensional model of the patient's vasculature from the patient specific image data; enable a user to mark the destination within the 3-dimensional model of the patient's vasculature; determine an access route from 1 or more entry points to the destination and analyse access route parameters; and, access a database storing data relating to physical properties of at least one catheter system and analyze the access route parameters against the physical properties of the at least one catheter system to determine a ranking of catheter systems suitable for navigating from an entry point to a destination.

In another embodiment, the method includes the steps of: enable selection of a catheter system and create a virtual model of a selected catheter system; co-register the virtual model of a selected catheter system with the 3-dimensional model of the patient's vasculature; enable user manipulation of the virtual model of a selected catheter system within the 3-dimensional model of the patient's vasculature via a mechanical to electrical interface.

In another embodiment, the mechanical to electrical interface includes a) a proximal end interface of physical catheter lines that includes a catheter and guide wire that can be coaxially moved and rotated within a vessel and b) a distal interface enabled to convert mechanical movement of the proximal end to electrical signals that provide input to the virtual model of a selected catheter system and the 3-dimensional model of the patient's vasculature.

In another embodiment, the method includes the steps of: access a machine learning database storing information relating to past procedures and; provide feedback to a user during user manipulation of the virtual model of a selected catheter system within the 3-dimensional model of the patient's vasculature based on a user's performance and pre-determined knowledge of the procedure as determined by the machine learning database.

In another embodiment, the method includes the steps of: access a machine learning database storing information relating to past procedures and; provide feedback to a user during user manipulation of a catheter system during a procedure based on a user's performance and pre-determined knowledge of the procedure as determined by the machine learning database.

In another embodiment, the method includes the steps of: prompt a user after a procedure has been completed to provide feedback to the machine learning database in a pre-determined format.

In another embodiment, the method includes the steps of: review a user's performance as determined by a comparison of pre-determined procedure parameters with actual procedure parameters as measured during the procedure; and display to a user a comparison of the user's performance to the pre-determined procedure parameters.

In another embodiment, the invention describes a method of analyzing the effectiveness of specific catheter equipment used in conducting surgical procedures where the surgical procedure includes navigating a catheter system through a patient's vasculature from an entry point to a destination, using a non-transitory computer readable medium encoded with instructions to perform the following steps: storing data from a plurality of surgical procedures conducted using catheter systems within specific patients, where the data includes: patient data used during a surgical procedure, the patient data including 3-dimensional data of a patient's vasculature through which a procedure was conducted; catheter system data relating to a specific catheter system used during a procedure including a plurality of physical properties of a catheter systems used during the procedure; and, performance data relating to the use of a catheter system during a procedure as related to the patient data; and analyzing a combination of the patient data, catheter system data and performance data to identify problem procedures and problem anatomical features in relation to specific catheter systems, procedure and patient data.

In another embodiment, the method includes: introducing a virtual catheter having defined physical properties into a 3-D model of a patient's vasculature having one or more problem anatomical features; and, evaluating the movement of the virtual catheter within the 3-D model of a patient's vasculature having one or more problem anatomical features to determine if the virtual catheter has superior or inferior physical properties as compared to a specific catheter system.

In yet another aspect, the invention provides a system for improving the efficiency of surgical procedures conducted using catheter systems, where the surgical procedure includes navigating a catheter system through a patient's vasculature from anentry point to a destination, the system including: an imaging scanner operable to obtain patient specific image data of the patient's vasculature; and a non-transitory computer readable medium encoded with instructions to perform the following steps: construct a 3-dimensional model of the patient's vasculature from the patient specific image data; enable a user to mark the destination within the 3-dimensional model of the patient's vasculature; determine an access route from 1 or more entry points to the destination and analyze access route parameters; and, access a database storing data relating to physical properties of at least one catheter system and analyze the access route parameters against the physical properties of the at least one catheter system to determine a ranking of catheter systems suitable for navigating from an entry point to a destination.

In another embodiment, the non-transitory computer readable medium is further encoded to: enable selection of a catheter system and create a virtual model of a selected catheter system; co-register the virtual model of a selected catheter system with the 3-dimensional model of the patient's vasculature; enable user manipulation of the virtual model of a selected catheter system within the 3-dimensional model of the patient's vasculature via a mechanical to electrical interface.

In yet another embodiment, the mechanical to electrical interface includes a) a proximal end interface of physical catheter lines that includes a catheter and guide wire that can be coaxially moved and rotated within a vessel and b) a distal interface enabled to convert mechanical movement of the proximal end to electrical signals that provide input to the virtual model of a selected catheter system and the 3-dimensional model of the patient's vasculature.

In another embodiment, the non-transitory computer readable medium is further encoded to: access a machine learning database storing information relating to past procedures; and, provide feedback to a user during user manipulation of the virtual model of a selected catheter system within the 3-dimensional model of the patient's vasculature based on a user's performance and pre-determined knowledge of the procedure as determined by the machine learning database.

In a still further embodiment, the non-transitory computer readable medium is further encoded to: access a machine learning database storing information relating to past procedures and; provide feedback to a user during user manipulation of a catheter system during a procedure based on a user's performance and pre-determined knowledge of the procedure as determined by the machine learning database.

In another embodiment, the non-transitory computer readable medium is further encoded to: prompt a user after a procedure has been completed to provide feedback to the machine learning database in a pre-determined format.

In one embodiment, the non-transitory computer readable medium is further encoded to: review a user's performance as determined by a comparison of predetermined procedure parameters with actual procedure parameters as measured during the procedure; and display to a user a comparison of the user's performance to the pre-determined procedure parameters.

In yet another aspect, the invention provides a system for analyzing the effectiveness of specific catheter equipment used in conducting surgical procedures where the surgical procedure includes navigating a catheter system through a patient's vasculature from an entry point to a destination, the system including a non-transitory computer readable medium encoded with instructions to perform the following steps: storing data from a plurality of surgical procedures conducted using catheter systems within specific patients, where the data includes: patient data used during a surgical procedure, the patient data including 3-dimensional data of a patient's vasculature through which a procedure was conducted; catheter system data relating to a specific catheter system used during a procedure including a plurality of physical properties of a catheter systems used during the procedure; and, performance data relating to the use of a catheter system during a procedure as related to the patient data; and analyzing a combination of the patient data, catheter system data and performance data to identify problem procedures and problem anatomical features in relation to specific catheter systems, procedure and patient data.

In one embodiment, the non-transitory computer readable medium is further encoded to: introduce a virtual catheter having defined physical properties into a 3-D model of a patient's vasculature having one or more problem anatomical features; and, evaluate the movement of the virtual catheter within the 3-D model of a patient's vasculature having one or more problem anatomical features to determine if the virtual catheter has superior or inferior physical properties as compared to a specific catheter system.

A method of creating a vasculature model of a patient and evaluating the movement of a modelled catheter through the vasculature model comprising the steps of:
  a. obtaining a series of 20 images of a volume of the patient, wherein each 20 image represents a planar slice of information through the patient at different levels;
  b. identifying vessel interiors and vessel boundaries of interest from the images of step a;
  c. assembling the vessel interiors and the vessel boundaries of interest from step b into a 3D assembly of vessel interior and vessel boundaries wherein the 3D assembly represents a 3D model of vessels of interest of the patient;
  d. interpolating between adjacent planar slices to create a continuous or substantially continuous representation of a vessel interior from one adjacent slice to another;
  e. introducing a modelled catheter into the 3D model where the modelled catheter is a finite element model representing the physical dimensions of a catheter and strength parameters of the catheter;
  f. enabling user manipulation of the modelled catheter within the 3D model to assess the viability of movement of the modelled catheter within the 3D model.

The method as in claim 29 where the 20 images are obtained via a computed tomography angiogram or a magnetic imaging resonance angiogram methodology.

The method as in claim 29 or claim 30 where the vessel boundaries are modelled to include adjustable properties reflecting vessel properties including stiffness and/or elasticity and wherein a user can adjust the vessel boundary properties prior to or during step f.

In another aspect, the invention provides a method of preparing for a recanalization procedure comprising the steps of:
  a. obtaining a series of 20 images of a volume of the patient, wherein each 20 image represents a planar slice of information through the patient at different levels;
  b. while diagnosing and/or preparing a patient for a recanalization procedure:
    i. identifying vessel interiors and vessel boundaries of interest from the images of step a;
    ii. assembling the vessel interiors and the vessel boundaries of interest from step b into a 3D assembly of vessel interior and vessel boundaries wherein the 3D assembly represents a 3D model of vessels of interest of the patient;

iii. interpolating between adjacent planar slices to create a continuous or substantially continuous representation of a vessel interior from one adjacent slice to another;

iv. introducing a modelled catheter into the 3D model where the modelled catheter is a finite element model representing the physical dimensions of a catheter and strength parameters of the catheter;

v. enabling user manipulation of the modelled catheter within the 3D model to assess the viability of movement of the modelled catheter within the 3D model.

In various embodiments, the modelled catheter is interfaced via a mechanical to electronic interface to a physical model of one or more proximal ends of a catheter system and wherein the user can manipulate the proximal ends to assess the viability of movement of the modelled catheter within the 3D model.

In one embodiment, the 3D model is built from a first region of the body to a second region of the body where the first region represents a region where the recanalization procedure is initiated and wherein a partially constructed 3D model is made available to enable user manipulation of the partially constructed 3D model.

In another embodiment, the method further includes the step of conducting data stream processing on a selection of 20 images to make available a usable 3D model or partially constructed 3D model to a user for manipulation within 6 minutes of completion of step a.

In another aspect the invention provides a method of preparing for a recanalization procedure comprising the steps of:

a. obtaining a series of 20 images of a volume of the patient, wherein each 20 image represents a planar slice of information through the patient at different levels;

b. analysing a selection of the 20 images to measure a plurality of anatomical features from the 20 images to obtain a series of anatomical measurements;

c. introducing the series of anatomical measurements into a patient vasculature database having a plurality of patient model records, each patient model record having a plurality of fields defining anatomical measurements and a corresponding patient 3D model;

d. identifying a best match patient model record based on a comparison of measured anatomical features from step b and a plurality of patient model records; and, e. enabling the user to access the corresponding patient 3D model from step d; and, f. while preparing a patient for a recanalization procedure enabling user manipulation of the patient 3D model to assess the viability of movement of a modelled catheter within the patient 3D model.

In one embodiment, the method includes following step a:

i. identifying vessel interiors and vessel boundaries of interest from the images of step a;

ii. assembling the vessel interiors and the vessel boundaries of interest from step b into a 3D assembly of vessel interior and vessel boundaries wherein the 3D assembly represents a 3D model of vessels of interest of the patient;

iii. interpolating between adjacent planar slices to create a continuous or substantially continuous representation of a vessel interior from one adjacent slice to another and form a current patient 3D model; and iv. enabling a user to access the current patient 3D model of step iii.

In another embodiment, the method includes the step of introducing a modelled catheter into the current patient 3D model.

In yet another embodiment, the method further includes the step of adding the current patient 3D model to the patient vasculature database as a new patient model record.

The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a schematic diagram of an embodiment of an apparatus configured to determine whether a catheter can be used to perform a particular task;

FIG. 4a is a schematic cross sectional view of a blood vessel through which a catheter is to be passed;

FIG. 4b is a schematic cross sectional view of a blood vessel through which a catheter is to be passed;

DESCRIPTION OF THE PREFERRED EMBODIMENTS

Introduction

Figure 1:
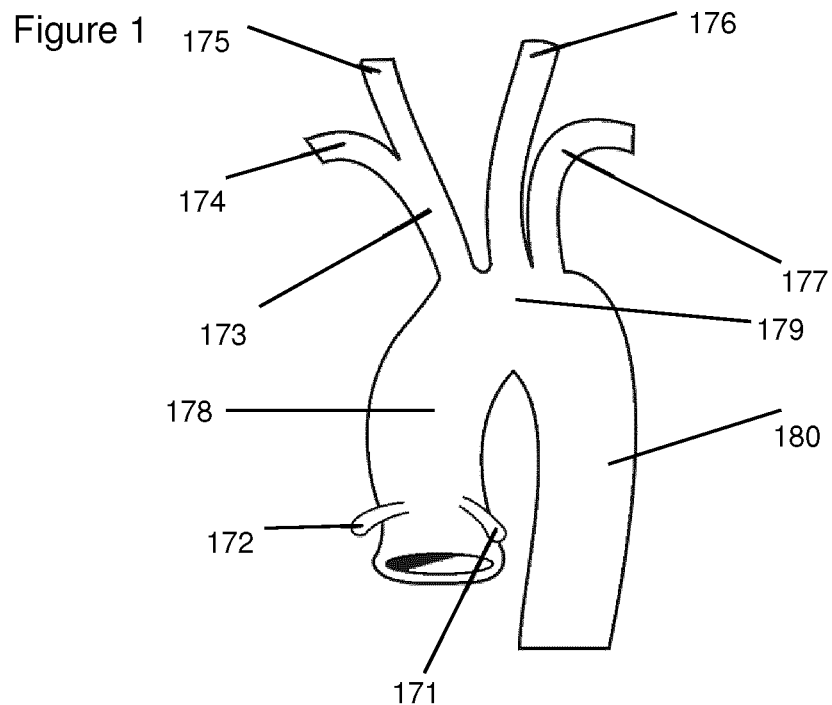
FIG. 1 is a perspective view of an aortic arch and associated blood vessels.

With reference to the figures there is described an apparatus configured to determine the route of a vessel line within a vessel in order to determine which (if any) vessel line can or should be used for a particular task.

All terms have definitions that are reasonably inferable from the drawings and description.

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

Apparatus Configuration

FIG. 3 shows a schematic of an apparatus that may be utilized to create a modelled vasculature of a patient that in conjunction with modelled catheters may be used for training and simulation purposes of medical procedures. More specifically, the apparatus may be used for determining an route (i.e. a pathway) for a modelled vessel line (MVL) (eg. a modelled catheter) through a modelled vasculature (MV). In particular, the modelled vasculature is preferably based on a scan of a patient where the scan may be a 3D scan such as a CT scan or an MRI scan that, post imaging, is manipulated to ascertain both the interior (lumen) of vessels as well as the vessel walls in 3D space.

In this case, the apparatus 300 comprises a scan data reader 301 configured to determine the course of a vessel within a body based on a scan of the vessel, memory 302 configured to store the physical properties of one or more vessel line; and a processor 303 configured to determine a route to reach a destination point within a MV using a MVL based on the determined vessel course, and whether it is possible to reach the destination point for each of the stored modelled vessel lines. The scan data reader may form part of the processor. A processor 303 may comprise one or more of, for example: a central processing unit (CPU); a microprocessor; a central processing unit contained on a single integrated circuit (IC); an application-specific integrated circuit (ASIC); an application-specific instruction set processor (ASIP); a graphics processing unit (GPU); a network processor, a microprocessor specifically targeted at the networking application domain; a multi-core processor.

Memory 302 may comprise one or more of, for example: a CD, a DVD, flash memory, a floppy disk, a hard disk, volatile memory, non-volatile memory or Random Access Memory.

It will be appreciated that the apparatus may also comprise a display and/or a user interface. A display may comprise one or more of, for example: a cathode ray tube or liquid crystal display (LCD); a computer screen; a smartphone screen; a tablet computer screen; a touchscreen; a projection screen; and a television screen. A user interface controller may comprise one or more of, for example, a touchscreen, a keyboard, a mouse, a joystick, and a touchpad.

The apparatus may be configured to interact with remote databases to populate the memory. The remote databases may be accessible via the internet. It will be appreciated that the memory, processor and display may not be part of a single computer. That is, the various components may be stored across several devices. For example, the database may be stored on a cloud computer. That is, the end user may have a client terminal which is configured to access a remote server which performs the scan calculations.

In this case, the scan data generally comprises information relating to the 3-dimensional structure of the vessel including the course of the vessel and the width of the vessel along that course.

Modelled Vessel Line and Vessel Line Parameters

There are a number of ways of modelling the vessel line (i.e. a catheter system) to facilitate routing a modelled vessel line through modelled vessels.

For example, the modelled vessel line can include physical properties that may comprise a combination of one or more of: thickness; transverse elasticity; longitudinal elasticity; transverse stiffness; longitudinal stiffness; resting configuration; and one or more activated configurations. Activated configurations may relate to the position of a modelled wire within a modelled catheter which may change the physical properties of the modelled catheter by changing, for example, its stiffness. It will be appreciated that these parameters may be given as a function of the length of the modelled vessel line. For example, the modelled vessel line may have a non-uniform stiffness profile by having a stiffer proximal portion and a more flexible distal portion.

Other ways of modelling the vessel line is to give minimum radii of curvatures for portions of the vessel line (corresponding to the maximum degree through which the vessel line can bend).

Figure 2A:
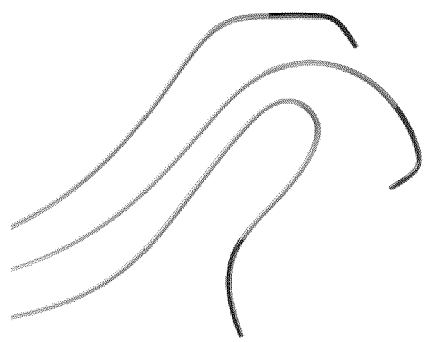
FIG. 2a is a view of a selection of three diagnostic catheters.
Figure 2B:
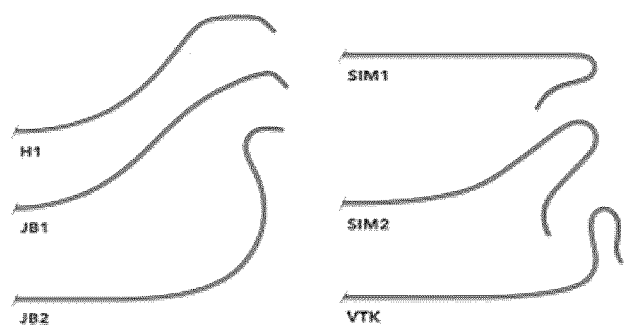
FIG. 2b is a view of a selection of six diagnostic catheters.
Figure 2C:
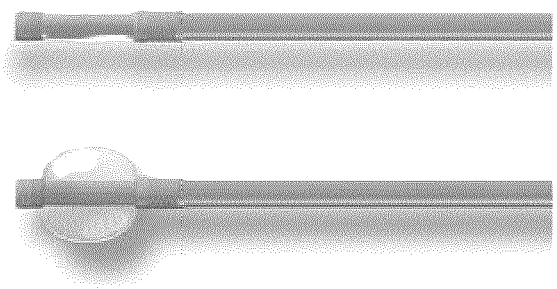
FIG. 2c is a view showing the end of a balloon catheter in a deflated configuration and in an expanded configuration.

In this case, the apparatus memory may store the vessel line parameters for the six representative and commercially known vessel lines shown in FIG. 2b labelled herein as H1, JB1, JB2, Simmons 1, Simmons 2 and VTK.

FIG. 4a-b shows a representative example a portion of a vessel 435. FIG. 4b is a sub-portion 435a of the vessel shown in FIG. 4a. In the portion of the vessel shown in FIG. 4a, the catheter 430 has to be routed through two vessel junctions 420, 421 in order to reach the desired destination point in order to perform the desired task (e.g. inserting a stent). For the purposes of illustration, FIGS. 4a-b can be considered to describe both an actual vessel and vessel line and a modelled vessel and modelled vessel line.

As a first stage, a scan of a vessel 435 or system of vessels is made (e.g. contrast CT angiogram scan or an MR angiogram) and read into the scan reader. The scan reader determines the course of the vessel 435 or system of vessels in 3D space. The course of the vessels may be considered to be the volume of vessels enclosed by the scanned vessel walls.

Hence, the modelled vessel may have coordinates defined in 3D space including boundary coordinates.

The steps utilized to achieve a modelled vessel may involve a number of different processors configured to read scan data, identify vessel boundaries within each image and assemble modelled vessels that can interact with a modelled vessel line (modelled catheter). In the case of a CT angiogram (CTA), digital 2 dimensional images representing different body planes are obtained which can be assembled into a 3 dimensional representation of the patient (eg. the cervical/cerebral regions of a patient). During processing to obtain a model vasculature, the raw CTA images are individually analyzed to identify key vessels and their boundaries and defined as such for subsequent 3D assembly. The vessels and boundaries from each individual image are assembled to form a 3D assembly with appropriate interpolation between images as may be fitted by interpolation algorithms. System checks including verification of data quality across images, x/y axis alignment may be performed to quality check the veracity of the 3D assembly. Other algorithms that filter or reduce raw data may form part of the system to improve processing times. Ideally, processing time to create a usable 3D model of a vasculature is sufficiently short to enable rapid assembly of a modelled vasculature such that the model is ultimately useful for the treatment of a patient. For example, it is preferred that the model becomes usable as part of the normal post processing of images as part of the diagnostic process and/or whilst a patient is being prepared for a procedure (eg. 10-15 minutes). That is, ideally, as soon as the raw CT images are being assembled for analysis, they will simultaneously be interpreted to build the 3D model of the vasculature. Thus, upon completion of the diagnostic analysis by the physician, when a decision to conduct a procedure is made, by that time or shortly thereafter, the 3D model is available for use (ideally the total time to create the 3D model or a partial 3D model range is in the range of about 4 minutes). Accordingly, as the patient is being prepared for the procedure, the surgeon will then be able to access and use the model and will have had a number of minutes available to work with the simulator prior to initiating the procedure when the patient is ready.

In situations where the processing time to complete a full model does not leave the surgeon with time to use the model before the patient has been prepared, the apparatus may be configured to build the model in a lower to upper direction and make a portion of the model available for use as it is being constructed. That is, the scan images of the aortic arch may be constructed into a partial model which becomes available before the cervical and cerebral images are fully processed, thus allowing the surgeon to evaluate/practice for this region of the procedure earlier. Having usable features of the model in less than 10 minutes, and preferably less than 6 minutes from the time of completing the CT scan is desirable.

Moreover, rapid data processing techniques may be employed including data windowing techniques that initiate model building based on select portions of data that together with approximating algorithms are used to predict and/or interpolate from that data so as to build the model. Such models may become more refined as the amount of data used to build the model is grown (i.e processed) but importantly allows for the model to can be used at an earlier stage.

Still further, the initial model available for the surgeon may be based on an approximation derived from past stored models within the system. For example, as the model database grows (ie. models from a number of patients), common features between a population of patients may provide means of characterizing such features as a continuum or partial continuum of common features. Such common features may include various physical parameters such as junction angles, diameters, volumes, radius of curvatures, etc. of major anatomical features (eg. aortic arch and the carotid arteries) all of which may be entered into a database so as to form a library of common features. As such, following the imaging of a patient, the system may prompt for or in some cases automatically determine values of such common features, search the database and find a previously stored model that best matches the current patient's features. As such, a best estimate model of the current patient's anatomy may be presented to and be usable to the surgeon while the model of the current patient is being constructed and refined. This may be particularly useful, at least on a preliminary basis, for making suggestions as to the best catheter to select to access the cervical arterial system.

The apparatus may also enable operator input to introduce options into the model. For example, a 3D modelled vasculature could be considered as fitting on a continuum between a rigid/inflexible system of vessels and boundaries (i.e. substantially rigid walls) to a flexible system having fully flexible vessels and boundaries that are deformable under various pressures. As such, the 3D modelled vasculature can include controls that allow the operator to adjust the behavior of a modelled vasculature based on various parameters such as age, disease (eg. atherosclerosis) and/or other medical conditions (eg. diabetes, hypertension, heart failure). Heart pulsatility may also be introduced into the model.

When the model is ready, the user will typically define a destination point 436 within the 3D model to where he wants to direct the modelled vessel line. This destination point 436 is indicated by a star in FIG. 4a. In this case, the user can define the destination point by interacting with a user interface displaying the modelled vessels and in various embodiments, the modelled vessel line. For example, the 3D scan may be displayed on a touch screen and the user can define the destination point by pressing on points corresponding to the desired destination point 436.

Route Determination

The processor 303 is configured to determine a route from an entry point through modelled vessels using a modelled vessel line. Generally, the entry point (eg. femoral, radial, brachial or carotid artery) will be predetermined or preselected depending on the particular vessel or task or procedure being used. That is, in most cases the entry point will be the femoral artery for cardiovascular or ischemic stroke procedures. However, it will be appreciated that in other embodiments, the user may define other entry points, or the apparatus may be configured to suggest one or more entry points based on the vessel course and the desired destination point.

As noted above, the apparatus is configured to determine a route to reach a destination point 436 within the modelled vessel 435 using a modelled vessel line 430 based on the determined vessel course. In most case, there will be only a limited number of routes available. That is, to reach the head, the route will normally comprise entering through the femoral artery, routing the vessel line up through the aortic arch and into the cervical and cerebral arteries. One possible exception is where the distal end of the vessel line is inserted into a junction not directly between the entry point and the destination point in order to configure the vessel line to enter the desired vessel. As will be discussed in more detail below, an example of this might be using the ascending aorta to return a Simmons catheter to its relaxed curved configuration.

The route may be defined simply by a central course/axis through the vessels between the entry point and the destination point. This may correspond to the location of the catheter when the modelled catheter is in position at the destination point. Alternatively, or in addition, the route may be defined as the position of a tip of the modelled vessel line as it moves between the entry point and the destination point. The route may also be summarized by listing the vessels which are chosen at each vessel junction. That is, if there are no junctions, the vessel line will proceed along the vessel until the destination point is reached. The route may be summarized or modelled as a series of one or more of: a pinch point; a vessel junction; and a vessel corner.

Modelled Catheter

As noted above, the apparatus is configured to determine whether it is possible to reach the destination point for each of the stored vessel lines (eg. the modelled catheters). For example, it will not be possible to reach the destination point if the modelled catheter cannot be manipulated from the entry point in such a way that a required junction turn cannot be made. For example, if the entry point is the femoral artery and the destination point is the common carotid artery, then it would not be possible to use a straight catheter if the straight catheter would not be able to make the turn from the aortic arch into the common carotid artery. Therefore the apparatus would determine that it is not possible to use such straight catheters to perform tasks which require access from the aortic arch into the common carotid artery. It will be appreciated that such a determination is patient specific and specific to the modelled catheter being tested within the system. For example, the junction between the common carotid artery and aortic arch in some patients may allow a straight catheter to be used which would not be possible in another patient with a differently configured aortic arch. In other cases, as a result of the angles between different vessels, the system may determine that only catheters having a complex curved tip will be able to traverse the junction.

The process of determining whether a modelled vessel line can move through a modelled vessel can be achieved by various mathematical algorithms and processes including finite element analysis (FEA) techniques and methods. In these methods, the modelled vessels and modelled vessel lines may be represented as discrete elements each of which may be mathematically defined as behaving in accordance with particular properties and/or in response to boundary or surface forces. In modelling a vessel line (eg. a catheter), the physical properties of the vessel line may be modelled along its length based on measured or predicted properties at different linear positions. For example, a 100 cm catheter may be modelled as having 3 primary zones such as a cerebral zone, cervical zone and thoracic zone, each representing the ultimate position of the catheter in the body during use. Each zone may be modelled as a discrete number of elements having various physical properties including both size and other parameters. The distal end (i.e. the cerebral zone) of a catheter may correspond to 16-20 cm of length of the catheter and be represented in 1 mm elements. Each 1 mm element may be modelled to include boundary conditions including outside diameter and inside diameter as well as physical properties such as transverse elasticity, longitudinal elasticity, transverse stiffness, longitudinal stiffness and resting configuration. The number of discrete elements may not be uniform along the length of the modelled catheter to the extend that the greatest variation in physical properties exists at the distal end of a catheter. The number of discrete elements can be modelled taking into account the correlation of the model's performance against a real world catheter as well as computing considerations as discussed below.

The process of building a model may involve evaluating an existing catheter using testing apparatus configured to measure the physical size of the catheter along its length as well as to probe and measure surface properties at different locations. Importantly, as many existing catheters may be constructed from proprietary formulations of polymers, manufacturers may not provide construction information or otherwise may not have this data and hence, must be measured for input into the model. After measuring the physical properties of a catheter, those properties may be included in the model. The veracity of the model may be tested against an existing catheter in standardized test vessels and standardized modelled vessels where the performance of both the existing and modelled catheters are compared to ensure appropriate correlation. Similarly, test vessels may be built that represent a reasonable range of anatomical situations that may be encountered during a procedure.

Determining whether it is possible to use a particular modelled vessel line for a particular route may also take into account the damage that would be caused by using the particular catheter in an actual procedure. For example, each patient may have a threshold force which may be tolerated on the walls of the vessels (alternatively a generic threshold may be used). If this threshold force is exceeded then it may be deemed that it is not possible to use this particular catheter in an actual procedure.

Based on the route and the 3D coordinates of the modelled vessels, certain measurements may be made. For example, the angle between the distal aortic arch (the pathway the catheter would come in from) and the proximal common carotid artery; and the origin of relevant vessel from the top of the aortic arch. These measurements may be used to determine which catheters may be used to perform the procedure. Such measurements may be automatically made or user-initiated. For example, certain junction measurements may be automatically displayed as an indicator to the surgeon on which the surgeon may make a decision. An automatic measurement may also be used as a basis for selecting or recommending one or more different catheters for an actual procedure as will be explained in more detail below.

Junction-Free Portion

FIG. 4b shows a junction-free curved portion of a vessel. In this case, the intermediate destination point is the end of the portion of the vessel. In this case, the catheter is a simple curved catheter.

For a junction-free curved portion of the vessel, the apparatus is configured to determine the deflection of the modelled vessel line from its relaxed position to go around the various turns in the modelled vessel. Based on the deflection and the stored stiffness parameters, the apparatus is configured to determine the forces which may be exerted on the vessel wall. Based on these forces, the apparatus is configured to determine whether inserting the catheter will damage an actual vessel.

It will be appreciated that one approximation of the force applied to the walls of the vessel is the static force applied when the catheter is at the destination position. Another approximation is to determine the force at particular sensitive points along the route (e.g. pinch points where the vessel is narrow and/or tight turns). In some embodiments, the apparatus may be configured to determine the force on various points on the vessel over a series of time points as the catheter is advanced along the determined route to the destination position. Determining the force at different times is particularly important for vessel lines which non-uniform stiffness profiles. For example, if the proximal end is stiffer than a distal end having a soft tip, then the soft tip may advance into the vessel but the stiffer more proximal part may not follow.

It will be appreciated that the apparatus may be configured to determine or estimate the resilience of the vessels themselves. This may be determined based on the scan (e.g. based on the tortuosity of the vessels) or based on patient-related data (e.g. age, gender, medical history including conditions such as diabetes or hypertension). Using a value for the resilience of the vessels may allow the apparatus to set a threshold force or deformation above which damage may occur. If too much damage would occur when passing the catheter through the determined route, this catheter may be discarded as a possible option for the procedure. Similarly based on previous experience and machine learning, it may be determined that for that degree of resilience and tortuousity, a given catheter will need to be discarded as a possible option for the procedure.

In addition, the apparatus may be configured to determine a measure of the difficulty to reach the destination point using a particular vessel line based on the physical properties of the particular vessel line and on the course of the vessel. For example, the level of difficulty may be based on a calculation of the forces exerted on the vessel wall when the vessel is being routed to the destination point. These forces may be calculated based on the stiffness of the vessel line as it navigates through the bends of the route. It will be appreciated that each vessel line may have a different stiffness profile and/or a different default configuration.

Another factor which may be taken into account is the manipulative steps required to guide the catheter along the determined route. For example, in a junction-free portion, a curved catheter may have to be rotated at each bend to align the curve of the catheter tip to the bend. This may require more complex manipulative steps than simply advancing a straight catheter. However, if the bends in the vessel are such that a straight catheter would cause damage to the vessel, it may be deemed that using a curved catheter is less difficult because although the manipulative steps are more complex, the risk of damage to the tissue is reduced.

In some embodiments, the overall difficulty may be the sum of the difficulties in navigating particular points along the route. As will be discussed below, this may allow the user to provide feedback into the system when carrying out procedures based on apparatus recommendations. That is, the user could enter difficulty numbers after performing a real procedure (e.g. the user could rate the difficulty in navigating the aortic arch as a 5/5 of a particular patient whereas the apparatus estimated it would be a 3/5). This may allow the apparatus to refine how the difficulty ratings are calculated to provide more accurate recommendations in future.

If particular configurations are consistently rated as being extremely tough, this may drive the need for innovation and coming up with new catheter designs and training modules to access these configurations as will be described in greater detail in relation to FIG. 7B.

Taking Junctions into Account

FIG. 4a shows a larger portion of the route where in addition to junction-free portions, there are two junction portions.

It will be appreciated that, in many cases, the key junction will be the aortic arch as there are a number of intersecting vessels here (a simplified version is shown here). That is, the aortic arch may be the limiting feature which defines whether it is possible to use a particular catheter and, if possible, how difficult it may be to use a particular catheter.

An important aspect of routing though junctions is the ability of the catheter tip to navigate out of the exit of one vessel (e.g. 420a or 421a) and into the entrance of the next vessel in the route (e.g. 420c or 421c) within the available space. As discussed in more detail below, there are a number of standard procedures for particular vessels which allow junctions to be navigated. In general, the parameters stored for each vessel line may include the range of vessel junction configurations which can be navigated by a particular vessel line. Vessel junction configurations may be described in terms of the vessel junction entrance (shape, area and orientation); vessel junction exit (shape, area and orientation); and volume around the vessel junction. For example, for a simple curved catheter, the stored vessel line parameters may define that the catheter can make an 80° turn from a vessel exit to a vessel entrance if the vessel exit and entrance each extend beyond a circle of 10 mm$^2$.

Vessel Junction Examples (1)

In many cases, a catheter simply follows a direct route from the entry point to the destination point (possibly with some external rotational manipulation to align a curved section with a vessel). For example, when the vessel line diameter is more than half the width of the diameter of the vessel at a particular point, there is limited scope for manipulating the vessel line other than advancing it along or retracting it from the vessel. However, for certain types of catheter, there may be more complex manipulations available in order to shape the catheter in such a way as to perform a particular task.

However, in large vessels or when using narrow vessel lines, there may be scope to perform more complex manipulations within the vessel. This is particularly the case with curved catheters which have a relaxed configuration in which the catheter is bent back on itself (e.g. Simmons or VTK catheters as shown in FIG. 2b).

Figure 5A:
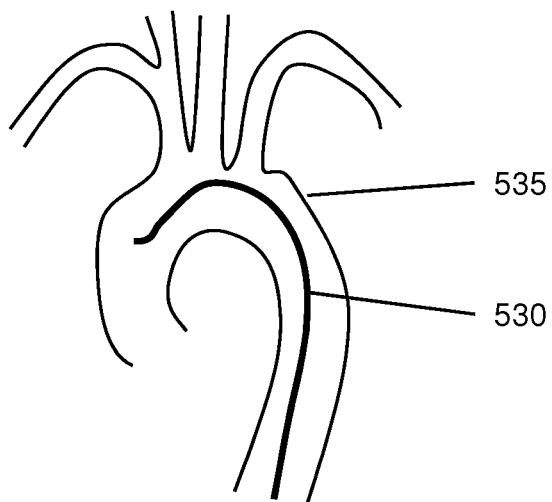
FIG. 5a is a view showing show the manipulation required to navigate a Simmons catheter from the aortic arch into the brachiocephalic artery.
Figure 5B:
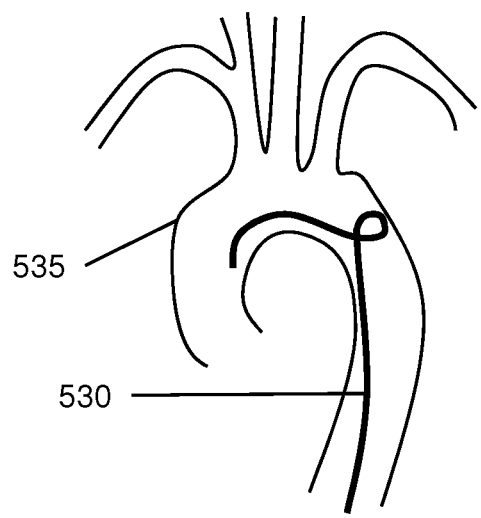
FIG. 5b is a view showing show the manipulation required to navigate a Simmons catheter from the aortic arch into the brachiocephalic artery.
Figure 5C:
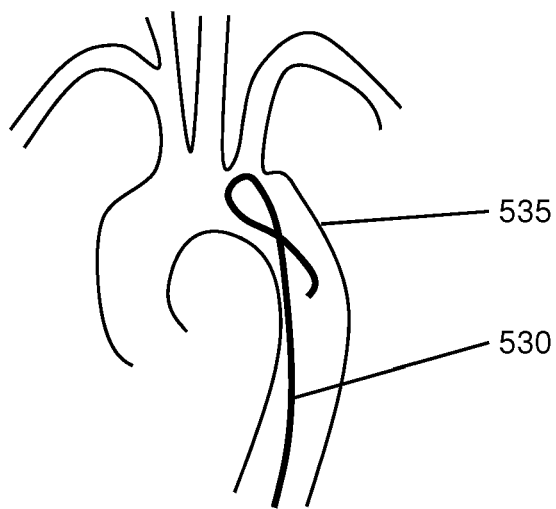
FIG. 5c is a view showing show the manipulation required to navigate a Simmons catheter from the aortic arch into the brachiocephalic artery.
Figure 5D:
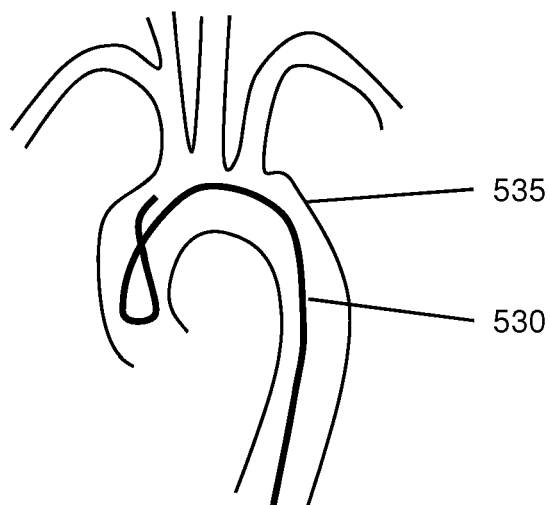
FIG. 5d is a view showing show the manipulation required to navigate a Simmons catheter from the aortic arch into the brachiocephalic artery.
Figure 5E:
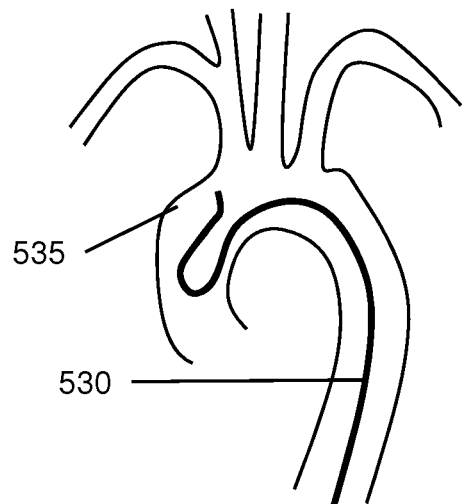
FIG. 5e is a view showing show the manipulation required to navigate a Simmons catheter from the aortic arch into the brachiocephalic artery.
Figure 5F:
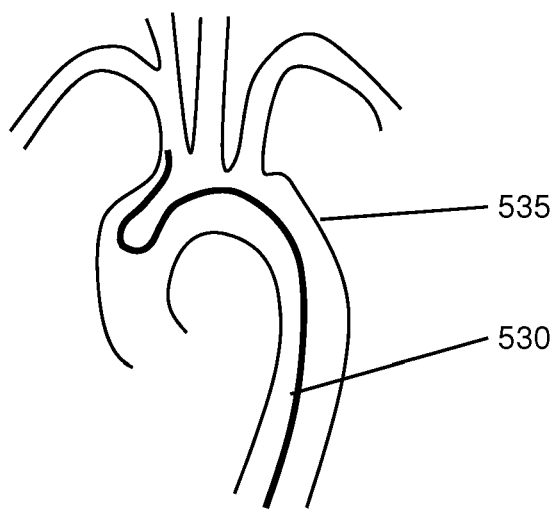
FIG. 5f is a view showing show the manipulation required to navigate a Simmons catheter from the aortic arch into the brachiocephalic artery.

For reference in relation to various procedure techniques, FIG. 5a-e shows a scissor technique which may be used to reform a Simmons catheter. A Simmons catheter 530 is shown in its relaxed configuration in FIG. 2b. FIG. 5a shows the scenario where a Simmons catheter has been advanced into the transverse aorta of a vessel 535. With the arch of the catheter over the aortic arch, the catheter is rotated rapidly to form a loop. This is shown in FIG. 5b. Continuing to the rotate the catheter causes the catheter to 'scissor' as the tip moves from the transverse aorta into the descending aorta. This is shown in FIG. 5c. Advancing the catheter causes the looped portion to enter into the ascending aorta as shown in FIG. 5d. Then the catheter is rotated in the opposite direction to return the distal portion of the catheter to its relaxed reverse-curved shape (FIG. 5e). The catheter can then be retracted to engage with one of the branching vessels from the aortic arch.

Figure 6A:
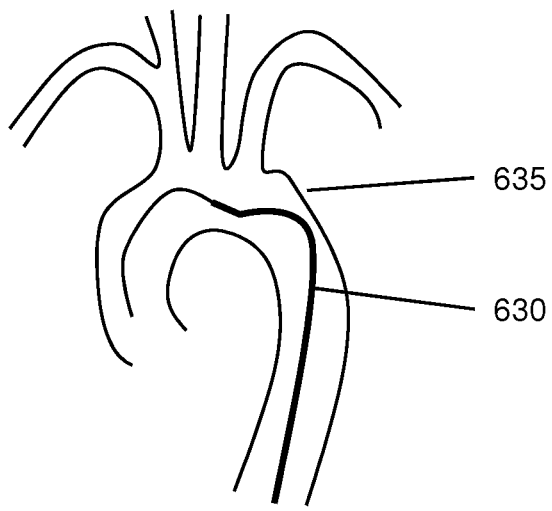
FIG. 6a is a view showing the manipulations required to navigate a VTK catheter from the aortic arch into the left common carotid artery.
Figure 6B:
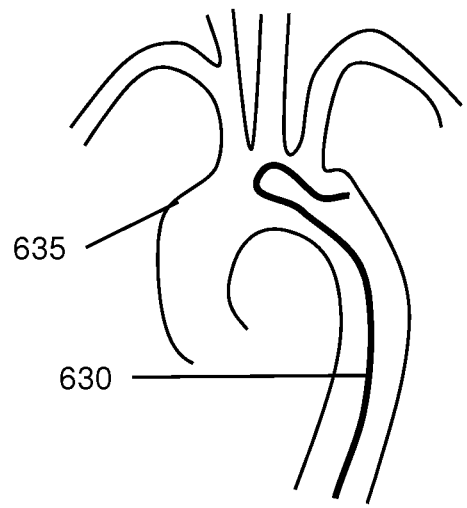
FIG. 6b is a view showing the manipulations required to navigate a VTK catheter from the aortic arch into the left common carotid artery.
Figure 6C:
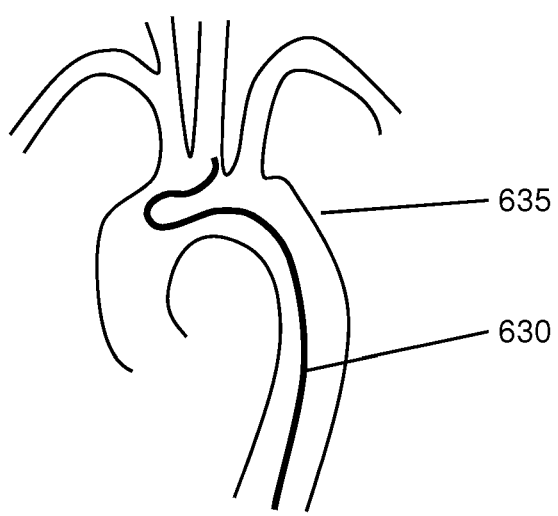
FIG. 6c is a view showing the manipulations required to navigate a VTK catheter from the aortic arch into the left common carotid artery.

FIG. 6a-c shows an alternative way of accessing vessels from the aortic arch. In this case, the vessel line is a VTK catheter which is shown in its relaxed configuration in FIG. 2b. In FIG. 6a, the vessel line 630 has been positioned in the descending aorta of the vessel 635 over a guide wire. Then, as shown in FIG. 6b, the guidewire is pulled back and the VTK catheter 630 is rotated to reform in the descending aorta. Then, as shown in FIG. 6c, the VTK catheter is advanced and rotated to engage with the carotid artery from the aortic arch.

The stored data for each vessel line may incorporate standard manipulations such as these and associated parameters which describe the circumstances in which the manipulations may be used. For example, associated with a Simmons catheter might be the range of positions of a vessel entrance which can be accessed using the scissors method shown in FIG. 5a-5f. In addition, the data may include information on the minimum volume within the descending aorta required to perform this manipulation. If this volume is not available, the processor may determine that a Simmons catheter cannot be used to perform the desired task.

In this way, the apparatus may be configured to provide tips and tricks at likely failure points e.g. with a VTK, the wire has to go really high and after hooking left common carotid artery with a VTK catheter, pull back slightly to engage it better before advancing the wire. Or, if there is a bovine arch (left common carotid artery arises from the innominate artery the apparatus may warn the physician of how the catheter will have a tendency to go towards the right side. Other potential tips and tricks may include: using information from the Computed Tomography Angiography (CTA) to see the carotid higher up (e.g. what is the bifurcation like, is there disease at carotid bifurcation?); determining if there are any risks to take the wire into the Internal Carotid Artery (ICA); determining if the External Carotid Artery (ECA) anterior or posterior on lateral angiography and/or taking the AP (Accessory Pathway) and lateral tube out of sync so that the AP tube looks at the arch and the lateral tube looks at the carotid bifurcation.

Output

The results of these determinations may be used in a number of ways. For example, the apparatus may simply provide feedback to the user regarding which vessel lines can be used for a particular task (e.g. defined by the destination point). Other embodiments may rank the available catheters based on predetermined criteria such as ease of external manipulations required to perform the task and/or the risk of vessel damage.

In other embodiments the apparatus may be configured to output results of determination to replicate the feedback provided by a scanner during a medical procedure. This may show what is the determined route and manipulation steps would look like in a real-time x-ray of the procedure. In addition, simulated scans may be adapted to provide an indication of the forces which would be applied to the vessel wall (e.g. acceptable force in green, potentially damaging force in red). This may help the interventionist to understand which parts of the vessel are most at risk from performing the procedure.

Some embodiments may be configured to determine the parameters for a better catheter for a particular task. For example, if the parameters of the best catheter already stored in the system results in excess force at a particular junction, the apparatus may be configured to suggest a more flexible catheter portion which has to pass that particular junction.

Other Options

It will be appreciated that the precise structure of the various vessels such as the aortic arch varies from patient to patient, so using scan data allows information (e.g. vessel junction configuration) to be used which is specific to the patient, and patient-specific guidance on which catheter to use may be provided. In addition, the apparatus may be configured to use real-time data from the patient thus providing a system and method for providing individualized medicine to the patient.

In other embodiments, the apparatus may be configured to provide a virtual model for training and/or output 3D design parameters to allow a 3D model of the vessel to be created for design and testing of vessel lines. This may also allow the user to practice the manipulative steps required to perform the procedure on a simulator (e.g. a virtual or 3D model) whilst the patient is being prepared. It will be appreciated that many of the procedures which would make use of apparatus and methods described herein are extremely time sensitive.

When determining how a modelled vessel line will interact with the modelled vessel, the apparatus may also be configured to determine the effect of the force of gravity; and/or the force of fluids on the vessel line (e.g. static pressure or fluid flow). Various parameters including the age of the patient may be factored into the 3D model to represent the real-world differences when conducting procedures on patients of different ages.

Machine Learning

The apparatus may be configured to store and use hundreds of angiograms and their 3D models and expert opinion to train the software to:
  Break up a particular situation in terms of level of difficulty e.g. on a scale of 1-5
  Provide recommended catheter shapes;
  Provide a simulation (e.g. in the form of a video) of how that catheter will likely play out in the real situation;
  utilize data from many procedures from multiple centers to identify common problems/solutions for improving system recommendations (i.e learning);
  Provide guidance on choice of wire and how high to take the wire to provide sufficient support; and/or
  Run simulations to show how the catheter could flip out if the wire is not high enough.

The apparatus may also allow the physician to build their own library of solutions in their own hands. This can be used to provide individualized feedback to a specific physician as well as the community at large. That is, first the physician can take guidance from the system. Then based on the guidance they can perform a real case. Based on the performance during the real case, the physician can provide feedback after the case to the system. For example, the physician could note that navigating through the aortic arch was more difficult than expected. The apparatus incorporates this information through machine learning so as to continue to improve the accuracy of guidance in the future. For example, based on feedback on how well the difficulty level prediction matched the user's experience, the apparatus may restrict or expand the range of junctions which can be navigated by a particular catheter. This input can be received from multiple centers around the world such that the collection and analysis of data can be on a broad scale and where the results of that analysis can be utilized by distributed users.

So, overall the apparatus is configured to provide a recommendation of what choice of vessel line works, and preferably an indication of which vessel line is likely to work the best. The apparatus may also provide guidance on things like how high to take the wire for sufficient support.

The apparatus may also provide a menu of catheters so that the interventionist can try and different one to see how it would likely play out in a simulation.

It will be appreciated that the apparatus may provide an environment for better catheter design for difficult arches and testing of the catheters in virtual and/or 3D printed models.

Figure 7:
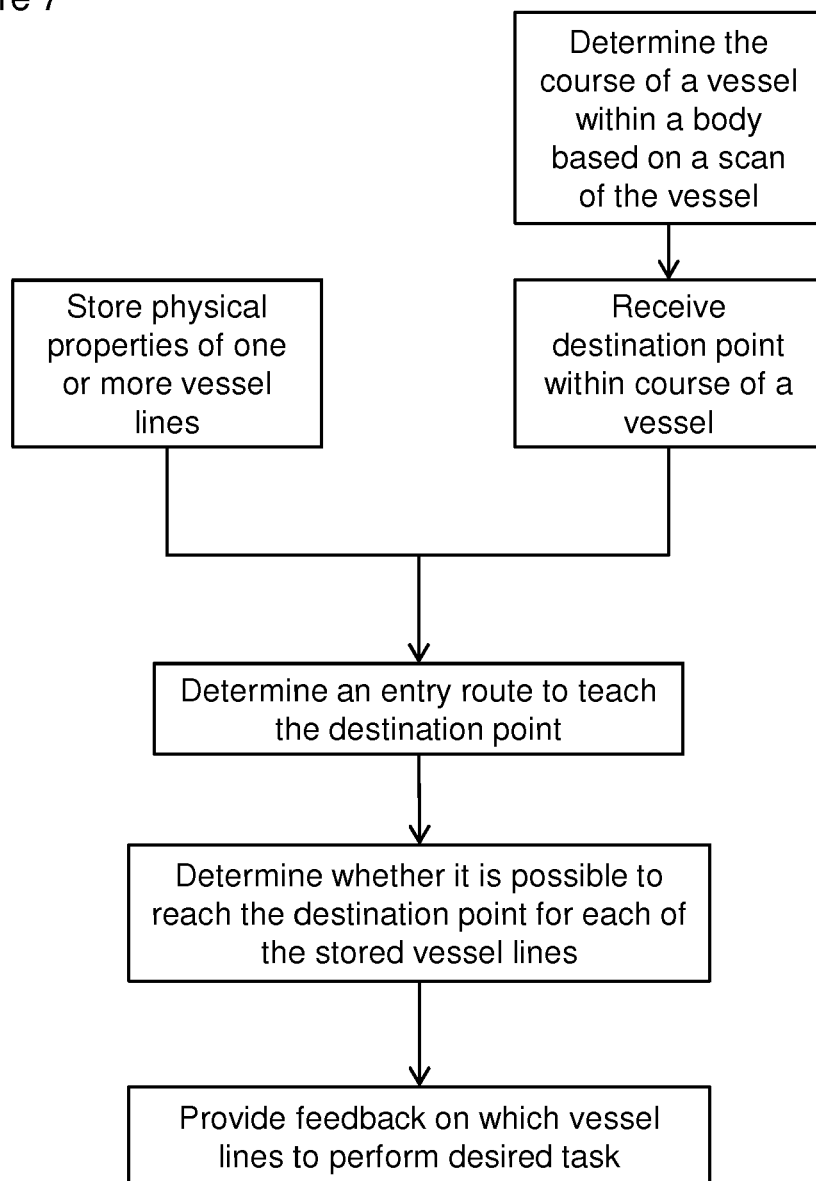
FIG. 7 is a flow diagram of a high level processing algorithm in accordance with one embodiment of the invention.
Figure 7A:
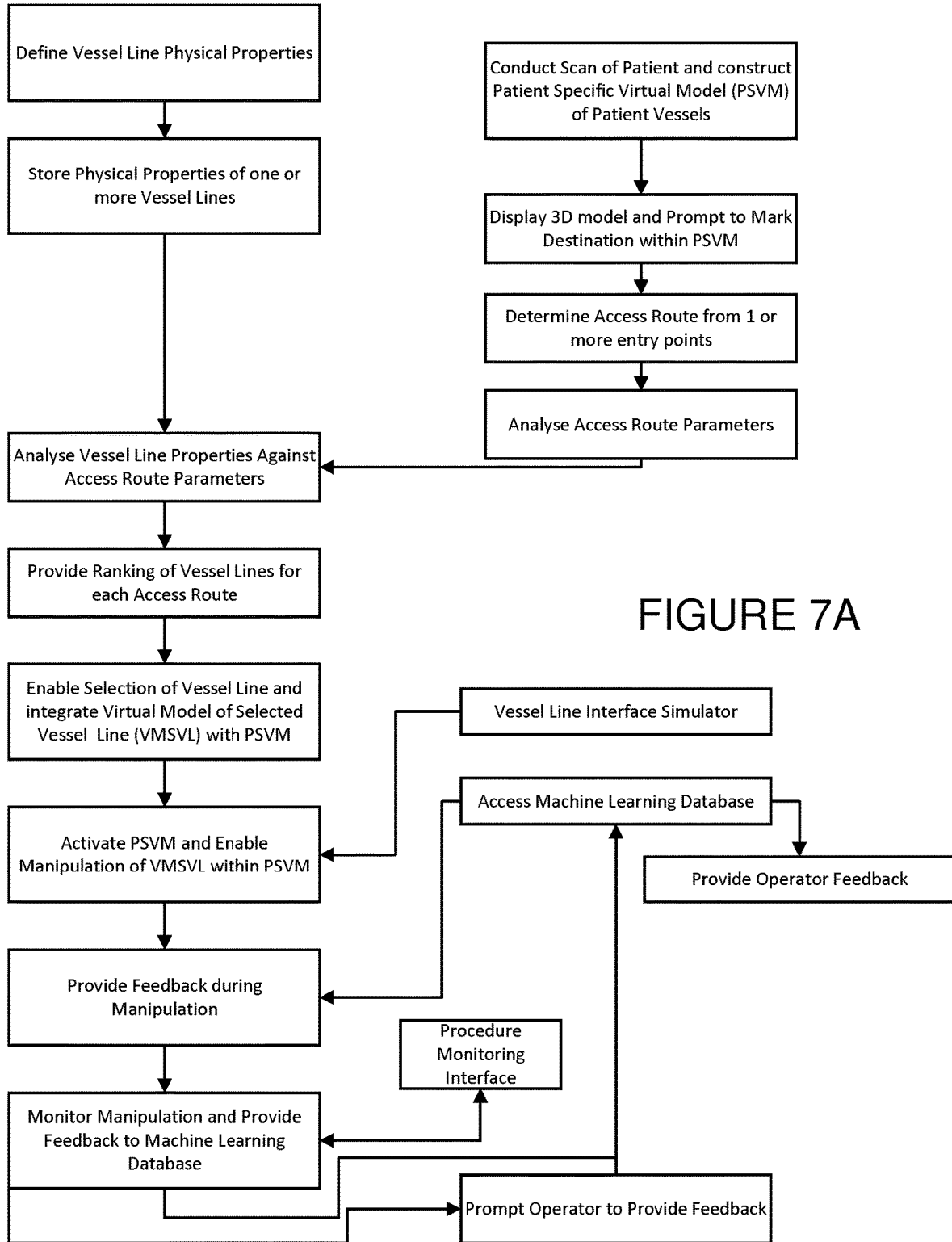
FIG. 7A is a flow diagram showing further details of a processing algorithm in accordance with one embodiment of the invention enabling feedback from a machine learning database during a procedure.
Figure 7B:
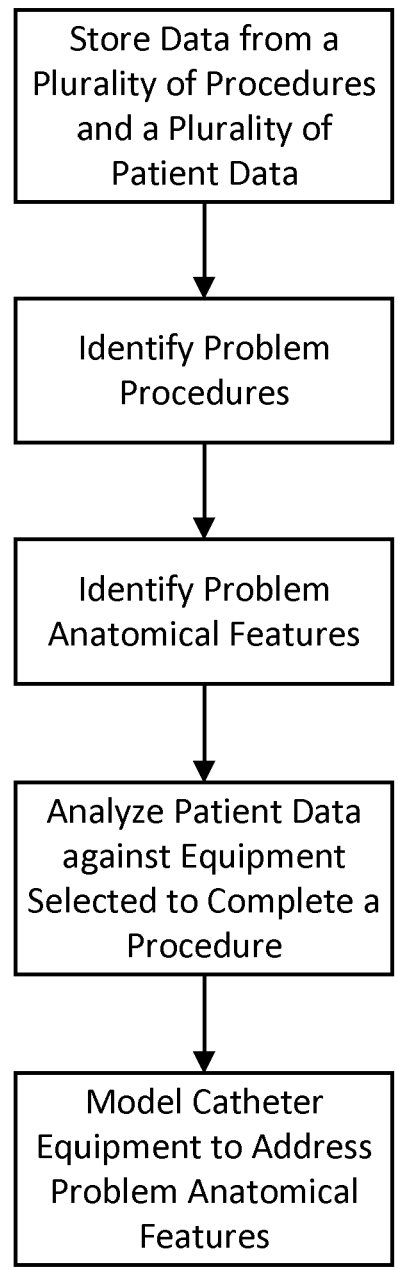
FIG. 7B is a flow diagram showing further details of a processing algorithm in accordance with one embodiment of the invention enabling data from a plurality of procedures to be analyzed to assist in the design of new access equipment.
Figure 7C:
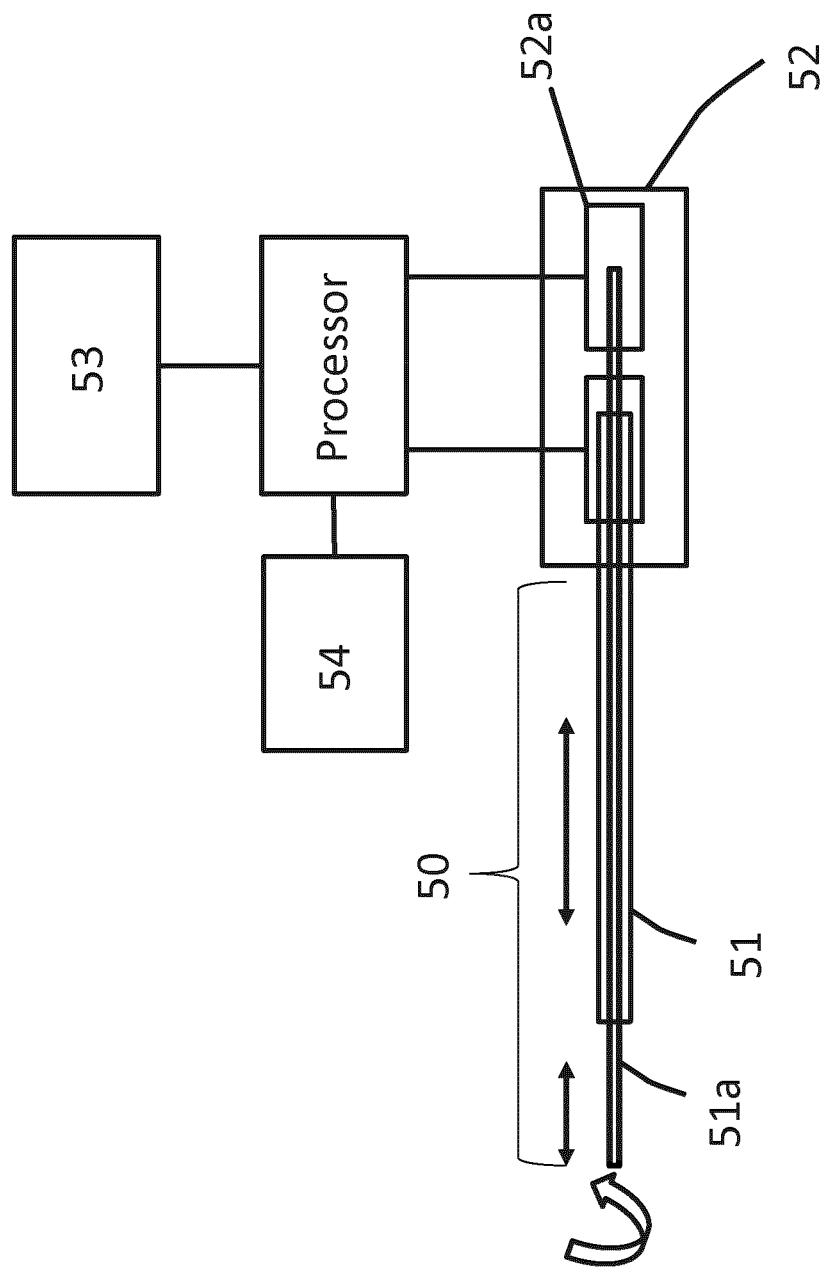
FIG. 7C is a schematic diagram showing a catheter simulation system in accordance with one embodiment of the invention.

In some embodiments, the 3D virtual model in the simulator may allow actual pushing and twisting of proximal ends of catheters and wires in the simulator while the resistance and behavior of the catheter and wire is simulated based on how a real catheter in the vessel would behave as described in relation to FIG. 7C.

In another embodiment, FIG. 7 shows a flow chart showing how the apparatus of FIG. 3 determines the route and which vessel lines to use based on the scan data, the desired destination point and vessel line parameters. As shown, a database may store the physical properties of one or more vessel lines. Imaging data from a patient may be used to create a 3D model of the patient's vasculature and specifically vessels of the upper thorax, neck and brain. Within the 3D model, the physician may be prompted to mark the destination (eg. a blood clot) within a vessel whereby the system may calculate a route from one or more entry points (eg. carotid access or femoral artery access). Physical property data from one or more vessel lines can then be used to determine the recommended vessel line from each entry point.

As shown in FIG. 7 A, the above general steps may be completed according to a representative methodology. More specifically, and as described above in relation to a simulator, imaging data from the patient may be utilized to construct a patient specific virtual model (PSVM) of the patient's vessels. The PSVM is displayed and the physician is prompted to mark a destination within the PSVM and the system may determine a route from one or more entry points. Once a route has been determined route parameters may be evaluated based on various parameters including geometry of the vessels and the age of the patient.

Thereafter, the route parameters may be analyzed against vessel line properties that have been defined and stored within a library/database of vessel lines. Based on this analysis, a ranking of preferred vessel lines can be displayed for one or more routes. The system may then enable the physician to select a vessel line and integrate a virtual model of a selected vessel line (VMSVL) with the PSVM.

The PSVM may be activated enabling the physician to manipulate the VMSVL within the PSVM. During this simulation, which may be conducted as a patient is being prepared, based on past data that may be stored in a machine learning database, the physician may be provided with feedback that may provide tips on the procedure to assist the physician. In one embodiment, as shown in FIG. 7e, an interface between the VMSVL and the user is provided by means of a vessel line interface 50. A vessel line interface generally includes a proximal end interface of physical vessel lines that includes a catheter 51 and guide wire 51a that can be coaxially moved and rotated within a simulated vessel from a 3D model 53. The physical vessel lines interface with the modelled vessel lines by means of an appropriate mechanical to electrical interface 52.

More specifically, each distal end of the simulation catheters 51, 51a are interfaced with a interface system 52 that measures axial movement (i.e. linear position), axial pressures and twisting (torque) being applied to the distal ends in addition to applying force feedback or resistance to these movements (haptics). The sensor system 52 is calibrated to interpret these movements in relation to the 3D model data 53 that represents the specific modelled vasculature within which the surgeon is practicing and provide a visual picture 54 of the catheter movement through the modeled vasculature on a monitor. By way of example, if the surgeon is manipulating the distal end of a simulation diagnostic catheter (for example a VTK) through an aortic arch based on a 3D data from imaging a real patient, the simulator will utilize the known properties of the VTK as a basis for displaying the movement on the monitor based on the boundary conditions of the 3D data of the patient's vasculature. That is, twisting and pushing forces being a pplied to the distal end will be translated to simulated movements of the tip on the monitor taking into account the properties of that particular catheter and where its simulated position is. For example, based on the position of the tip of the catheter at a junction, pushing on the catheter may not advance its position due to the simulated tip being in contact with a boundary. In this case, the system may provide force feedback to the user suggestive of contact of the simulated tip against the boundary. Similar calculations and modelling can be conducted for twisting movements as well. Accordingly, surgeons can practice their techniques across a wide range of patient anatomies (based on those stored in the database) utilizing a wide range of different catheters (having modelled properties). Importantly, the system can also be used in real surgical situations, where after a patient's image data has been obtained, the corresponding 3D data can be uploaded to the simulator as described above and, where based on a comparison to previously stored image data, one or more catheters can be recommended as useful for a particular anatomy based on similarities between patients, but also allow the surgeon to "practice" with one or more catheters prior to the actual procedure on the patient. Typically, such practice would be conducted while a patient is being prepared for the procedure. This can be an effective tool in enabling the procedure to be conducted more efficiently when it is actually initiated as the surgeon will have a better idea of which catheters may be best for that patient and they have just practiced manipulation of that catheter within the simulator. Similarly, this can be an effective tool for training and in particular understanding failure points during a procedure, understanding forces and tolerances and how they are influenced by anatomy. Further still, the simulator can be effective in learning hand motions for the surgeon.

In addition, the system may, during the actual procedure as it is being conducted, be used to monitor the performance of the physician during the procedure including parameters such as time to gain access to the neck vessels based on the selection of a specific catheter as that may then be compared to previous procedures that may have been conducted on previous patients having a similar anatomy. Such monitoring can be added to the machine learning database to improve the machine learning database performance for future procedures. A procedure monitoring interface may detect the movement of a catheter system during the procedure in relation to the patient specific virtual model and may be co-registered with x-ray data (explained below).

In addition, a physician may also provide their specific feedback to the machine learning database when they have completed the procedure in accordance with one or more pre-determined feedback protocols. For example, input may be conducted manually after a procedure.

In another embodiment, the PSVM may be co-registered with x-ray data obtained during the procedure in 3D space such that the physician can "see" the vessels during the procedure. That is, during current procedures, the physician utilizes x-ray data that provides definition to radio-opaque bodies such as bones, the catheter and guide wire. By combining and superimposing (i.e co-registration) of the PSVM and x-ray data, the physician will be able to better visualize the location of the catheter system during the procedure. In this case, anatomical landmarks (eg. tip of nose or other landmarks) obtained from original diagnostic imaging can be superimposed with real time data obtained during a procedure, such that data recorded from a simulation can be used during the procedure to assist the surgeon in determining the position of anatomical features. For example, during a procedure, the absence of contrast can make identification of various features difficult. However, feedback from a simulated practice run can be used to assist in determining a position even when there is no contrast present based on the superimposition of data.

As shown in FIG. 7B, in another aspect, the system may as described above, store data from a plurality of procedures and a plurality of patient data for the purposes of analyzing and recognizing problems for the objective of improving or contributing to the design of new equipment. That is, from the data, problem procedures may be identified either from data automatically collected during a procedure and/or by physician input. From the procedure data, problem anatomical features may be identified and analyzed against equipment selected to complete the procedure. This analysis is then used to model equipment that may be used to overcome the problem anatomical feature, which can then be used to identify the features/properties of new equipment that could be designed to overcome that identified problem.

The same procedures can also be applied to other difficult anatomical situations in other parts of the body such as but not limited to: heart, kidneys, leg and arm vessels.

Other features can be incorporated. These can include:

Modelling patient conditions into the model. In this case, patient conditions including age related conditions such as hypertension, atherosclerosis and/or spine shortening or other conditions such as diabetes. That is, the simulator may allow for the physician to input weighting factors that may adjust the model's behavior. For example, if the surgeon knows the patient is over 75, an age-related weight may be applied to the 3D model boundaries such that the surgeon can practice/simulate catheter movement in stiffer vessels. Such parameters may be adjustable so that the surgeon can practice incorporating a variety of different parameters.

In one embodiment, the simulator can accommodate access from different locations including the femoral artery, radial artery, brachial artery and direct puncture of the carotid artery. In some cases, the anatomical features of the aortic arch may be that access through the aortic arch will be very difficult or not possible. As such, the simulator may be able to determine and recommend access through another route when such conditions are recognized. In some cases, recommendations of the safest spot to access a carotid artery may be recommended.

Various patients may also have somewhat unique situations and based on the machine learning from a wide range of patients, these situations can be recognized and guidance provided. Such conditions may include:

a. Internal carotid artery is occluded. This is not that uncommon. When a surgeon recognizes this condition, the difficult part of the procedure is to get past the occluded artery since it cannot be seen. However often on the CT scan there is some observed calcification such that the surgeon cannot see the unopacified artery on the source images of the CT scan. Using these a potential 'shadow' of where the vessel would be expected can be created to aid with simulation and muscle memory.

b. An aneurysm may be encountered on the way to reach the clot. Aneurysms are dangerous and if not recognized can rupture and produce significant complications. As such, the simulator may be able to recognize them and make recommendations for avoidance.

c. Other unusual anatomical variations. These can include variations in the fetal posterior artery, the persistent trigeminal artery, the large anterior choroidal artery or early bifurcation of the middle cerebral artery, all of which is presented and identified to the surgeon could assist in preventing delays during a procedure.

Still further, the simulator may be used to assist at common decision points during a procedure. Based on known anatomical data from previous patients, recommendations can be made to use or not use specific catheter systems such as a balloon guide catheter or a distal access catheter.

While specific embodiments of the invention have been shown and described in detail to illustrate the application of the principles of the invention, it will be understood that the invention may be embodied otherwise without departing from such principles.

What is claimed is:

1. A method of analyzing the effectiveness of specific catheter equipment used in conducting surgical procedures where the surgical procedure includes navigating a catheter system through vasculature of a patient from an entry point to a destination, the method comprising the steps of:

using a non-transitory computer readable medium encoded with instructions to perform the following steps:

storing data from a plurality of past surgical procedures conducted using catheter systems within past patients, where the data comprising:

patient data, stored in a patient vasculature database, the patient data including three-dimensional data of a patient's vasculature through which a past surgical procedure was conducted;

modelled catheter system data relating to a specific catheter system used during a past surgical procedure including a plurality of modelled physical properties of catheter systems used during the past surgical procedure; and performance data relating to the use of a catheter system during past surgical procedures as related to the patient data;

analyzing a combination of the patient data, modelled catheter system data and performance data to identify problem procedures and problem anatomical features in relation to specific catheter systems, procedures and patient data;

a. obtaining a series of 2D images of a volume of a new patient, wherein each 2D image represents a planar slice of information through the new patient at different levels;

b. analyzing a selection of the 2D images to measure a plurality of anatomical features from the 2D images to obtain a series of anatomical measurements;

c. introducing the series of anatomical measurements into the patient vasculature database having a plurality of patient model records, each patient model record having a plurality of fields defining anatomical measurements and a corresponding patient 3D model;

d. identifying a best match patient model record based on a comparison of measured anatomical features from step b and a plurality of patient model records;

e. enabling a user to access the corresponding patient 3D model from step d; and f. while preparing a patient for a recanalization procedure enabling user manipulation of the patient 3D model to assess the viability of movement of a modelled catheter within the patient 3D model.

2. The method as in claim 1 further comprising the step of:

introducing a virtual catheter having defined physical properties into a 3-D model of a patient's vasculature having one or more problem anatomical features; and evaluating the movement of the virtual catheter within the 3-D model of vasculature of a patient having one or more problem anatomical features to determine if the virtual catheter has superior or inferior physical properties as compared to a specific catheter system.

3. The method as in claim 1, wherein following step a, further comprising the following steps:

i. identifying vessel interiors and vessel boundaries of interest from the images of step a;

ii. assembling the vessel interiors and the vessel boundaries of interest from step b into a three-dimensional assembly of vessel interior and vessel boundaries wherein the three-dimensional assembly represents a three-dimensional model of vessels of interest of the patient;

iii. interpolating between adjacent planar slices to create a representation of a vessel interior from one adjacent slice to another and form a current patient three-dimensional model; and iv. enabling a user to access the current patient three-dimensional model of step iii.

4. The method as in claim 3, further comprising the step of introducing a modelled catheter into the current patient three-dimensional model.

5. The method as in claim 4, further comprising the step of adding the current patient three-dimensional model to the patient vasculature database as a new patient model record.

6. The method as in claim 5, wherein the modelled catheter is interfaced via a mechanical to electronic interface to a physical model of one or more proximal ends of a catheter system and the user can manipulate the proximal ends to assess the viability of movement of the modelled catheter within the current patient three-dimensional model and the patient three-dimensional model.

* * * * *